US010692606B2

(12) United States Patent
Bender et al.

(10) Patent No.: US 10,692,606 B2
(45) Date of Patent: Jun. 23, 2020

(54) STRESS LEVEL REDUCTION USING HAPTIC FEEDBACK

(71) Applicant: International Business Machines Corporation, Armonk, NY (US)

(72) Inventors: Michael Bender, Rye Brook, NY (US); Gregory J. Boss, Saginaw, MI (US); Jeremy R. Fox, Georgetown, TX (US); Albert Avetisian, Bayside, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/168,374

(22) Filed: Oct. 23, 2018

(65) Prior Publication Data
US 2020/0126670 A1    Apr. 23, 2020

(51) Int. Cl.
*G16H 50/30* (2018.01)
*A61B 5/00* (2006.01)
*G06F 3/01* (2006.01)

(52) U.S. Cl.
CPC ........... *G16H 50/30* (2018.01); *A61B 5/6802* (2013.01); *A61B 5/7267* (2013.01); *A61B 5/74* (2013.01); *G06F 3/016* (2013.01)

(58) Field of Classification Search
None
See application file for complete search history.

(56) References Cited

U.S. PATENT DOCUMENTS 9,251,809 B2    2/2016  Bender et al.
9,300,925 B1 *  3/2016  Zhang ................... H04N 7/181
9,762,719 B2 *  9/2017  Tartz ...................... G06F 3/005
2015/0061825 A1 * 3/2015  Suzuki .................... H04W 4/21
                                                              340/5.52
2017/0010672 A1 * 1/2017  Tanaka ................... H04W 12/06
(Continued)

FOREIGN PATENT DOCUMENTS

WO    WO2016097376 A1    6/2016

OTHER PUBLICATIONS

Giakoumis et al., "Subject-dependent biosignal features for increased accuracy in psychological stress detection." International Journal of Human-Computer Studies, Nov. 2012, pp. 425-439.

(Continued)

*Primary Examiner* — Carlos Garcia
(74) *Attorney, Agent, or Firm* — Brian M. Restauro, Esq.; George S. Blasiak, Esq.; Heslin Rothenberg Farley & Mesiti PC

(57) ABSTRACT

Methods, computer program products, and systems are presented. The method computer program products, and systems can include, for instance: obtaining biometric data of a first user, the first user using a first client computer device associated to the first user; returning a current stress level classification of the first user in dependence on a processing of the biometric data; generating feedback data in dependence on the current stress level classification of the first user, the feedback data including haptic response feedback data; and sending the feedback data to a second client computer device of a second user to present feedback to the second user, the feedback being in dependence on the current stress level classification of the first user and including haptic feedback.

20 Claims, 12 Drawing Sheets

(56) References Cited

U.S. PATENT DOCUMENTS

2017/0011210 A1* 1/2017 Cheong ............... A61B 5/0022
2017/0135635 A1* 5/2017 Bostick ................ A61B 5/681
2018/0060757 A1* 3/2018 Li ....................... G06K 9/6256

OTHER PUBLICATIONS

De Vries et al., "Insightful Stress Detection from Physiology Modalities using Learning Vector Quantization." Elsevier, vol. 151, Part 2, Mar. 2015, pp. 873-882.
Han et al., "Detecting work-related stress with a wearable device." Elsevier, vol. 90, Sep. 2017, pp. 42-49.
Kelling et al., "Good Vibes: The Impact of Haptic Patterns on Stress Levels," *AcademicMindtrek2016—Proceedings of the 20th Academic Mindtrek Conference*. Oct. 17, 2016, pp. 130-136.
Zubair et al. 2015. "Smart Wearable Band for Stress Detection". IEEE. *2015 5th Int. Conf. on IT Convergence and Security (ICITCS '15)*. Aug. 2015. pp. 1-4.
Anonymous. "Biometric Monitoring, Alerting, Reporting and Analysis of Contact Center Agents". IPCOM000230019D. Published on Aug. 13, 2013. 2 pages.
Anonymous. "Method and System for Monitoring and Managing Stress Level of Agents in a Call Center" IPCOM000202349D. Published Dec. 14, 2010. 3 pages.
Pechenizkiy et al. 2011. "What's Your Current Stress Level? Detection of Stress Patterns from GSR Sensor Data". IEEE. Published in *2011 IEEE Int. Conf. on Data Mining Workshops*. Presented circa Dec. 11, 2011. Published Feb. 9, 2012. On pp. 573-580.

* cited by examiner

STRESS LEVEL REDUCTION USING HAPTIC FEEDBACK

BACKGROUND

Location based services (LBS) are software services that use location data to control functionality of computer systems LBS information services have a number of uses, e.g. in social networking, entertainment, security, and in a plurality of additional applications. LBS services employ location services for locating mobile computer systems. Location services can incorporate a variety of different locating service technologies such as the Global Positioning System (GPS), cellular network locating technologies, and WI-FI based locating technologies, and other technologies. One example of an LBS is a location based messaging services wherein notifications and other messages to users can be in dependence on the respective locations of the users.

Data structures have been employed for improving operation of computer system. A data structure refers to an organization of data in a computer environment for improved computer system operation. Data structure types include containers, lists, stacks, queues, tables and graphs. Data structures have been employed for improved computer system operation e.g. in terms of algorithm efficiency, memory usage efficiency, maintainability, and reliability.

Artificial intelligence (AI) refers to intelligence exhibited by machines. Artificial intelligence (AI) research includes search and mathematical optimization, neural networks and probability. Artificial intelligence (AI) solutions involve features derived from research in a variety of different science and technology disciplines ranging from computer science, mathematics, psychology, linguistics, statistics, and neuroscience.

SUMMARY

Shortcomings of the prior art are overcome, and additional advantages are provided, through the provision, in one aspect, of a method. The method can include, for example: obtaining biometric data of a first user, the first user using a first client computer device associated to the first user; returning a current stress level classification of the first user in dependence on a processing of the biometric data; generating feedback data in dependence on the current stress level classification of the first user, the feedback data including haptic response feedback data; and sending the feedback data to a second client computer device of a second user to present feedback to the second user, the feedback being in dependence on the current stress level classification of the first user and including haptic feedback.

In another aspect, a computer program product can be provided. The computer program product can include a computer readable storage medium readable by one or more processing circuit and storing instructions for execution by one or more processor for performing a method. The method can include, for example: obtaining biometric data of a first user, the first user using a first client computer device associated to the first user; returning a current stress level classification of the first user in dependence on a processing of the biometric data; generating feedback data in dependence on the current stress level classification of the first user, the feedback data including haptic response feedback data; and sending the feedback data to a second client computer device of a second user to present feedback to the second user, the feedback being in dependence on the current stress level classification of the first user and including haptic feedback.

In a further aspect, a system can be provided. The system can include, for example a memory. In addition, the system can include one or more processor in communication with the memory. Further, the system can include program instructions executable by the one or more processor via the memory to perform a method. The method can include, for example: obtaining biometric data of a first user, the first user using a first client computer device associated to the first user; returning a current stress level classification of the first user in dependence on a processing of the biometric data; generating feedback data in dependence on the current stress level classification of the first user, the feedback data including haptic response feedback data; and sending the feedback data to a second client computer device of a second user to present feedback to the second user, the feedback being in dependence on the current stress level classification of the first user and including haptic feedback.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
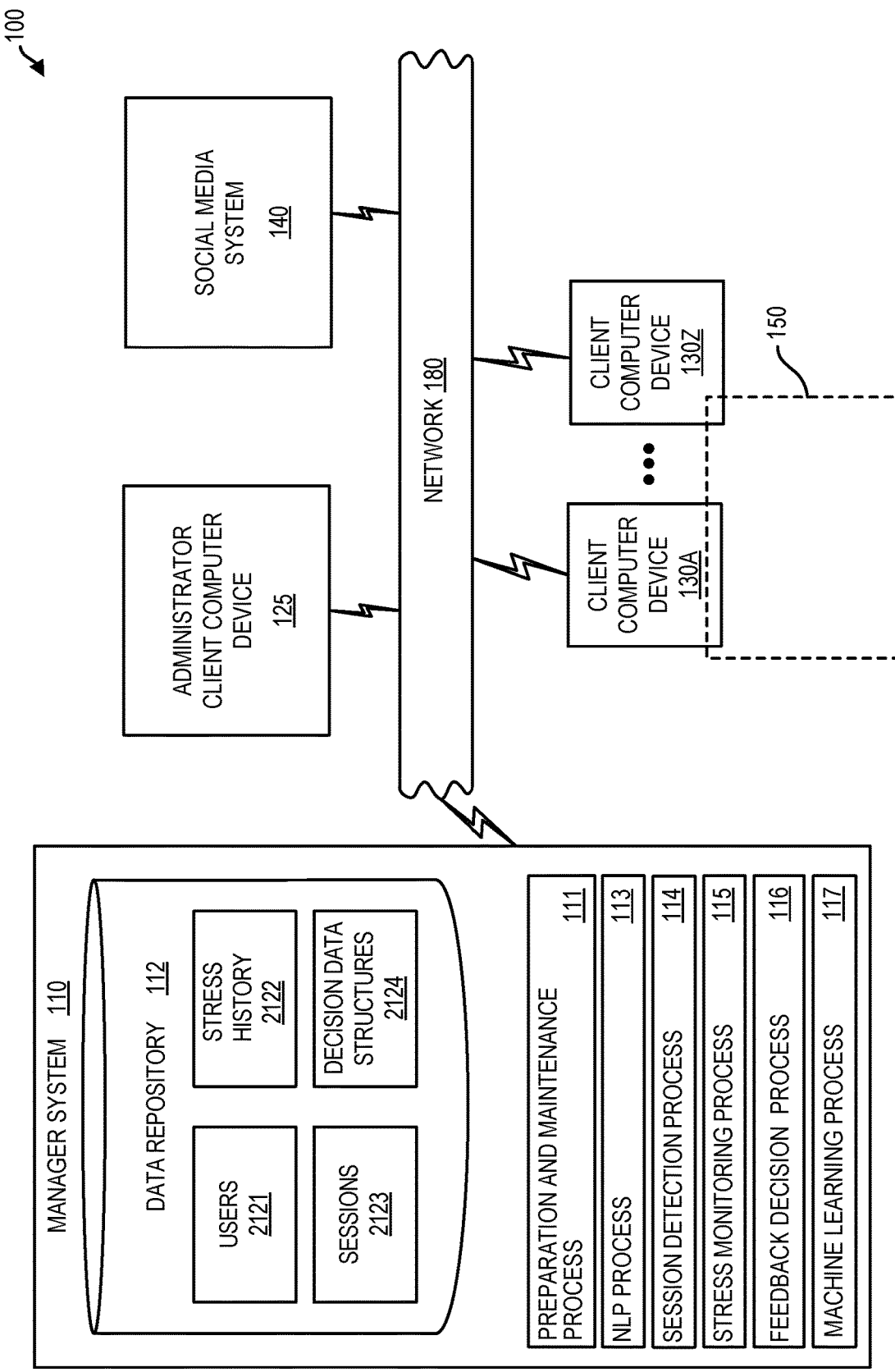
FIG. 1 is a block schematic diagram of a system having a manager system, client computer devices, and administrator client computer device, and a social media system.

System 100 for use in reducing stress of a user shown in FIG. 1. System 100 can include manager system 110 having an associated data repository 112 client computer devices 130A-130Z administrator client computer device 125 and social media system 140. Manager system 110, client computer devices 130A-130Z, administrator client computer device 125, and social media system 140 can be in communication with one another via a network 180.

System 100 can include numerous devices which can be computing node based devices connected by network 180. Network 180 can be a physical network and/or a virtual network. A physical network can include, for example, a physical telecommunications network connecting numerous computing nodes or systems such as computer servers and computer clients. A virtual network can for example combine numerous physical networks or parts thereof into a logical virtual network. In another example, numerous virtual networks can be defined over a single physical network.

According to one embodiment, manager system 110 can be external to client computer devices 130A-130Z, administrator client computer device 125, and social media system 140. According to another embodiment, manager system 110 can be co-located with one or more client computer devices 130A-130Z, administrator client computer device 125, and social media system 140. Each client computer device 130A-130Z can also include one or more program to facilitate use of client computer devices 130A-130Z in system 100. Such one or more program can be installed in response to an installation package being received from manager system 110.

A client computer device of client computer devices 130A-130Z, according to one embodiment, can be a computing node device provided by a client computer e.g. a mobile device e.g. a smartphone, tablet, laptop, smartwatch, or PC that runs one or more program e.g. including a web browser for opening and viewing web pages. Each of the different client computer devices 130A-130Z can be associated to a different user. Regarding one or more client computer device 130A-130Z, a computer device of one or more client computer device 130A-130Z in one embodiment can be a computing node based device provided by a client computer, e.g. a mobile device, e.g. a smartphone or tablet, a laptop, smartwatch or PC that runs one or more program, e.g. including a web browser for opening and viewing web pages.

Social media system 140 can include a collection of files, including for example, HTML files, CSS files, image files, and JavaScript files. Social media system 140 can be a social website such as FACEBOOK® (Facebook is a registered trademark of Facebook, Inc.), TWITTER® (Twitter is a registered trademark of Twitter, Inc.), LINKEDIN® (LinkedIn is a registered trademark of LinkedIn Corporation), or INSTAGRAM® (Instagram is a registered trademark of Instagram, LLC). Computer implemented social networks incorporate messaging systems that are capable of receiving and transmitting messages to client computers of participant users of the messaging systems. Messaging systems can also be incorporated in systems that that have minimal or no social network attributes. A messaging system can be provided by a short message system (SMS) text message delivery service of a mobile phone cellular network provider, or an email delivery system. Manager system 110 can include a messaging system in one embodiment. During a process of registration wherein a user of system 100 registers as a registered user of system 100, a user sending registration data can send with permission data defining the registration data a permission that grants access by manager system 110 to data of the user within social media system 140. On being registered, manager system 110 can examine data of social media system 140 e.g. to determine whether first and second users are in communication with one another via a messaging system of social media system 140. A user can enter registration data using a user interface displayed on a client computer device of client computer devices 130-130Z. Entered registration data can include e.g. name, address, social media account information, other contact information, biographical information, background information, preferences information, and/or permissions information e.g. can include permissions allowing manager system 110 to query data of a social media account of a user provided by social media system 140 including messaging system data and any other data of the user. According to one embodiment, each of a care giver user and a care recipient user can grant permission to manager system 110 to query data of social media system 140 so that manager system 110 can query data of a conversation (e.g. text based and/or voice based) between the care recipient user and the care giver user.

Data repository 112 can include users area 2121, stress history area 2122, sessions area 2123, and decision data structures area 2124. Manager system 110 can run preparation and maintenance process 111, natural language processing (NLP) process 113, session detection process 114, stress monitoring process 115, feedback decision process 116, and machine learning process 117.

Data repository 112 in users area 2121 can store data on users of system 100. Users of system 100 can be registered users of system 100 who register for services provided by system 100. Services provided by system 100 can include services to reduce a stress level of users of system. Users of system 100 can take on various roles. Roles that can be assumed by users of system 100 can include a care-recipient user role and a caregiver use role. Over the course of deployment of system 100, a given user can transition from a care-recipient role to a caregiver role e.g. can transition from being a patient in a scenario where the user receives healthcare treatment; that same user can transition to a role where the user acts as a caregiver user e.g. where that same user happens to be a healthcare professional providing healthcare services to other users or, for example, where that same user is a parent who provides guidance to a user who is a child of the certain user in a care-recipient role. On registration into system 100, manager system 110 can allocate to a new registrant a unique universal identifier (UUID). In response to registration request of a user, manager system 110 can send an installation package to a client computer device of the user for installation on the client computer device. The installation package facilitates processes for the support of services provided by system 100. During the process of registration, a user sending registration data can send with permission data defining the registration data a permission that grants access by manager system 110 to data of the user within social media system 140. On being registered, manager system 110 can examine data of social media system 140 e.g. to determine whether first and second users are in communication with one another via a messaging system of social media system 140.

Data repository 112 in stress history area 2122 can record a history of stress experienced by users of systems 100. Stress levels can be generated by processing biometric data of users. Biometric data can be provided e.g. by one or more biometric sensor such as a camera sensor for use in sensing facial expressions of a user, a pulmonary sensor, such as a heart rate pulse or EKG sensor, and/or an EEG sensor for use in sensing brain activity, or another type of biometric sensor. Manager system 110 for generating a stress level classification based on biometric data can determine a variance of biometric data for a certain user relative to a baseline value for a certain biometric parameter. Manager system 110 can over time determine a baseline value for a biometric data parameter value e.g. including by averaging biometric data parameter values over time and can return a biometric variance value as a difference between a current biometric data parameter value and the determined baseline biometric data parameter value. Manager system 110 can generate biometric variance data and biometric data baseline values for a certain user using an output of one or more biometric sensor, e.g. can generate biometric variance data and biometric data baseline values for a certain user using an output of one biometric sensor (e.g. one pulmonary sensor, one camera sensor, one EEG sensor), or can generate biometric variance data and biometric data baseline values for a certain user using output of a plurality of biometrics sensor (e.g. one or more pulmonary sensor, one or more camera sensor, and/or more EEG sensor). Where biometric data is provided by spatial image data output by a camera sensor, the image data can be processed for return of sentiment parameter values, e.g., a "negative" sentiment parameter value in the range of 0.0 to 1.0 wherein a baseline value can be calculated for an individual to be a value of 0.5 (neutral sentiment over time).

Manager system 110 can return stress classifications for users based on the variance data for example can return a classification of "stressed" when the variance value exceeds a threshold value. Manager system 110, according to some embodiments, can return multiple stress level classifications e.g. according to one embodiment, two classification levels of stress, e.g. "stressed" and "not stressed" or, in one embodiment, three classification levels of stress e.g. "highly stressed," "stressed," or "not stressed," wherein the various stress level classifications are all in dependence on a return current variance value exceeding a threshold value. In one embodiment, manager system 110 can provide an N stress level classification system where N>3.

Data repository 112 and stress history area 2122 can store for each user of system 100, a stress history. The stress history for each user can include time-stamped variance values for each user. The variance values being difference values between a current biometric data parameter value and a baseline biometric parameter value for a certain biometric parameter for the certain user. The stress history values for each user can be time-stamped, as well as geo-stamped indicating a location of a client computer device when generating biometric data used to determine biometric variance values and stress level classifications. Biometric data processed by manager system 110 for return of biometric variance data can be biometric data, output from one or more biometric sensor e.g. a camera-based camera sensor for facial recognition sensing, a pulmonary sensor or an EEG sensor. One or more biometric sensor for output of biometric data can be incorporated into a client computer device 130A-130Z of a given user.

Stress history area 2122 can include biometric variance values that are time stamped and, therefore associated to times, and can also be geo-stamped and, accordingly, can be associated to locations. A client computer device incorporating a biometric sensor, at a time of output of biometric data by biometric sensor can tag output biometric data with a timestamp and geo-stamp specifying time and location of biometric data output. For such functionality a client computer device 130A-130Z can include a clock and location sensing capability. A client computer device can be configured to output location data indicating location of itself e.g. can include global positioning sensor (GPS sensor), sensing a location of the client computer device based on processed radio signals from a set of orbiting satellites. Manager system 110 can receive location data specifying a location of a client computer device from an location service that uses such methodologies as triangulation and time of flight to determine a client computer device's location based on received radio signals, received by a connection node e.g. a wireless local area network or a wireless cellular network.

Stress history area 2122, according to one embodiment, can store in a table UUIDs specifying users of system 100 associated to one or more biometric data value and/or biometric variance data value that is time stamped and/or geo-stamped. Biometric variance values can be timestamped and geo-stamped according to biometric data from which such values are derived. Manager system 110 in stress history area 2122 can further associate the time-stamped and/or geo-stamped biometric variance values context data. The context data can include, for example, speech data that specifies spoken words spoken to a care-recipient user the time-stamp times of the various biometric variance values. Manager system 110 can process voice data transmitted by a messaging system of social media system 140 and can return text specifying the content of a voice communication by application of a speech to text process. Speech data can be time stamped so that it is associated to a user having recorded biometric variance values. In such manner, biometric variance values, from which stress level classifications can be derived, can be associated to speech data presented to the user the varied specified times at which different and changing stress level classifiers for the user are returned.

Manager system 110 in sessions area 2123 can store data on sessions of system 100 mediated by manager system 110. A session can be characterized by a first user in a caregiver role providing guidance to a second user in a care-recipient role. Manager system 110 can employ various methodologies for determining commencement and determination of a session e.g. can determine that a session has been commenced when first and second users are in location proximity of one another. System 100 can provide location based services so that a session is determined to be commenced and/or terminated based on respective locations of one or more of first and second users. Manager system 110 according to one embodiment can detect that a guidance session has commenced when a care-recipient user breaches a geofence such as geofence 150 as depicted in FIG. 1. Manager system 110 according to one embodiment can detect that a session has commenced when first and second users have entered into a state in which they are in location proximity with one another e.g. within a designated threshold distance of one another. Manager system 110 can detect commencement of a session, according to one embodiment, when first and second users enter into a state in which they are in communication with one another e.g. using a messaging system e.g. which can be provided by social media system 140. Sessions data stored in sessions area 2123 can include e.g. start and stop times of a guidance session and participants of a session e.g. first and second users being specified with a UUID, as well as context data associated to a session.

Management system 110 in decision data structures area 2124 can store decision data structures for use in returning data decisions, performed by manager system 110, e.g. data decisions regarding a type of feedback to be provided by a user in response to manager system 110 processing of biometric variance data.

Manager system 110 running preparation and maintenance process 111 can prepare data for storage into data repository 112 for use by various remaining processes run by manager system 110 such as processes 113-118.

Manager system 110 can run NLP process 113 to process data for preparation of records that are stored in data repository 112 and for other purposes. Manager system 110 can run a Natural Language Processing (NLP) process 113 for determining one or more NLP output parameter of a message. NLP process 113 can include one or more of a topic classification process that determines topics of messages and output one or more topic NLP output parameter, a sentiment analysis process which determines sentiment parameter for a message, e.g. polar sentiment NLP output parameters, "negative," "positive," and/or non-polar NLP output sentiment parameters, e.g. "anger," "disgust," "fear," "joy," and/or "sadness," or other classification process for output of one or more other NLP output parameters, e.g. one of more "social tendency" NLP output parameter or one or more "writing style" NLP output parameter.

By running of NLP process 113 manager system 110 can perform a number of processes including one or more of (a) topic classification and output of one or more topic NLP output parameter for a received message (b) sentiment classification and output of one or more sentiment NLP output parameter for a received message or (c) other NLP classifications and output of one or more other NLP output parameter for the received message.

Topic analysis for topic classification and output of NLP output parameters can include topic segmentation to identify several topics within a message. Topic analysis can apply a variety of technologies e.g. one or more of Hidden Markov model (HMM), artificial chains, passage similarities using word co-occurrence, topic modeling, or clustering. Sentiment analysis for sentiment classification and output of one or more sentiment NLP parameter can determine the attitude of a speaker or a writer with respect to some topic or the overall contextual polarity of a document. The attitude may be the author's judgment or evaluation, affective state (the emotional state of the author when writing), or the intended emotional communication (emotional effect the author wishes to have on the reader). In one embodiment sentiment analysis can classify the polarity of a given text at the document, sentence, or feature/aspect level—whether the expressed opinion in a document, a sentence or an entity feature/aspect is positive, negative, or neutral. Advanced sentiment classification can classify beyond a polarity of a given text. Advanced sentiment classification can classify emotional states as sentiment classifications. Sentiment classifications can include the classification of "anger," "disgust," "fear," "joy," and "sadness."

Manager system 110 running session detection process 114 can include manager system 110 monitoring for the commencement of a guidance session in which a caregiver user provides guidance to a care-recipient user in which the caregiver user by his or her actions can increase or decrease a level of stress being experienced by the care-recipient user.

Manager system 110 running session detection process 114 can perform detection of session commencement and can also perform detection of session termination. Manager system 110 for detecting session commencement and/or session termination can examine location data associated to client computer devices 130A-130Z. Manager system 110 running session detection process 114 can include manager system 110 monitoring location data associated with client computer devices 130A-130Z and can detect that a guidance session has commenced when a first user e.g. a care-recipient user based on location data of their respective client computer device has breached a geofence 150 as depicted in FIG. 1. Manager system 110 running session detection process 114 can include manager system 110 monitoring location data associated with client computer devices 130A-130Z and can detect that a guidance session has commenced when first and second users based on location data of their respective client computer devices have entered into a state of being in proximity to one another e.g. are within a threshold distance of one another. Manager system 110 running session detection process 114 can examine data of social media system 140, and according to one embodiment, can examine messaging service data of social media system 140. Social media system 140 can include one or more messaging system e.g. a text based messaging system, an email based messaging system, or voice e.g. VOIP data messaging system. Manager system 110 can detect commencement of a guidance session based on first and second users being in communication with one another via a messaging system of social media system 140.

Manager system 110 to detect that a guidance session has terminated can examine location data of a first client computer device e.g. of a care-recipient user has exited a geofence such as geofence 150. Manager system 110 to detect that a guidance session has terminated can examine location data of the first and second client computer devices and can determine that a guidance session is terminated based on the first and second users entering into a state where the first and second users are spaced apart from one another by more than a threshold distance. Manager system 110 can determine that a guidance session has terminated based on an examination of messaging system data and can determine that a guidance session has terminated based on message data between first and second users defining a conversation terminating.

Manager system 110 can be configured so that obtaining of biometric data of one or more biometric sensor e.g. from a care-recipient client computer device for return of stress level classifications is activated in response to a session being commenced and can be further configured to that in response to a session being terminated, manager system 110 can terminate the obtaining of such data for return of stress level classification data. In such manner the collection of data is restricted to the collection of the most relevant data and memory and processing resources are conserved.

Manager system 110 running stress monitoring process 115 can monitor and process biometric data received from client computer devices 130A-130Z for respective users of the client computer devices 130A-130Z and can process the received biometric data to return biometric variance data. For return of biometric variance data, manager system 110 can process received biometric data for establishing and maintaining biometric baseline data for each user, e.g. based on an average of biometric data parameter values over time. Manager system 110 can return a biometrics variance value for a user based on a difference between a current biometric data parameter value and a baseline biometric data parameter value for a given biometric parameter. In dependence on returned biometric variance data values, manager system 110 can return stress level classifications. According to one embodiment, manager system 110 running stress monitoring process 115 can return a stress level within one of two stress level classifications e.g. a stressed classification and unstressed classification, where a stressed classification is determined based on biometric variance data values exceeding a stress indicating threshold. Manager system 110, according to some embodiments, can return multiple stress level classifications e.g. according to one embodiment, two classification levels of stress, e.g. "stressed" and "not stressed" or, in one embodiment, three classification levels of stress e.g. "highly stressed," "stressed," or "not stressed," wherein the various stress level classifications are all in dependence on a return current variance value exceeding a threshold value. In one embodiment, manager system 110 can provide an N stress level classification system where N>3 in dependence on biometric variance data values exceeding defined thresholds.

Manager system 110 running feedback decision process 116 can return feedback data which feedback data can be sent to client computer devices of client computer devices 130A-130Z. According to one embodiment, feedback data can include haptic feedback data which, when received by a client computer device, results in the client computer device activating a haptic response. Client computer devices 130A-130Z can include haptic output device e.g. vibration output devices which result in a client computer device vibrating on receipt of haptic feedback data. According to one embodiment, manager system 110 in response to a determination of a stress level classification of a care-recipient user can send to a caregiver user haptic response feedback data which when received by the caregiver user, users of client computer device results in the client computer device of the caregiver user vibrating based on the level indicated by the haptic response feedback data. The client computer device of a caregiver user can vibrate in dependence on a stress level classification that can be specified within haptic response feedback data e.g. can vibrate a smaller amount where the haptic response feedback data indicates that a care-recipient user is experiencing a moderate level of stress and can vibrate strongly when haptic response feedback data indicate that a care-recipient user is experiencing a higher level of stress, based on the described haptic response, a caregiver user can be made aware in real time as to a care-recipient users current level of stress and accordingly can take responsive measures to reduce the care-recipient user's level of stress.

Manager system 110 running feedback decision process 116 can return feedback data for sending to client computer devices provided by other than haptic response data. The feedback data can include e.g. text and/or voice data that prompts the caregiver user to take specified action in response to an output of stress monitoring process 115. Manager system 110 running feedback decision process 116 can include manager system 110 sending feedback data to a client computer device of a caregiver user with a text or voice based message specifying topics for presentment e.g. verbally by the caregiver user to the care-recipient user for reducing a current level of stress of a care-recipient user.

During the course of deployment of system 100, a predictive model for predicting a users stress level in response to presentment of classified topics to the user can be iteratively trained by machine learning. Such a predictive model, once trained by machine learning, can be configured to respond to query data in which candidate topics are specified as query data to returned predicted stress levels, in response to the candidate topics.

Manager system 110 running feedback decision process 116 can iteratively query a predictive model with various candidate topics and can examine returned data, returned from the predictive model that specifies stress level classifications associated to the various topics and can return as a topic for presentment by a caregiver user a topic predicted to yield reduced stress on the part of a care-recipient user.

Manager system 110, running feedback decision process 116, can send feedback data including e.g. text and/or voice based data specifying topic data to a client computer device of a caregiver user wherein the topic data includes one or more topic determined by querying of a predictive model to reduce a stress level of a care-recipient user. In response to a received prompt specifying a stress-reducing one or more topic, the caregiver user can present the one or more topic to a care-recipient user e.g. by verbal communication.

Manager system 110 running machine learning process 117 can train one or more predictive model for use by manager system 110 in returning predictions e.g. such as the described prediction of a returned stress level of a user in response to a presented topic. For training of a predictive model there can be applied as training data to the predictive model stress level classifications for stress level time segments associated to a conversation topic dataset. Through the course of deployment of system 100, manager system 110 can segment time into time segments for a user based on detected transitions in stress level classifications for the user e.g. when a user transitions from a stress level classification of being unstressed to a stress level classification of being stressed and then to a stress level classification of being highly stressed, depending on the classification methodology used. For each stress level classification time segment, manager system 110 can input as training data to a predictive model the stress level classification associated to the stress level time segment and a topic dataset e.g. comprising one or more topic, associated to the stress level time segment.

Embodiments herein recognize that stress level exhibited by a certain user can be in dependence on interactions of others with the certain user. Accordingly, embodiments herein set forth provide feedback to a caregiver user so that the caregiver user interacts with a certain user in a manner that reduces a stress level of the certain user. Feedback data sent to a caregiver user can include e.g. haptic response feedback data which can control a haptic response of a caregiver user of a client computer device and/or can include non-haptic response feedback data e.g. which can include text and/or voice prompt data which prompts a caregiver user to interact with a certain user in accordance with a particular manner.

Figure 2:
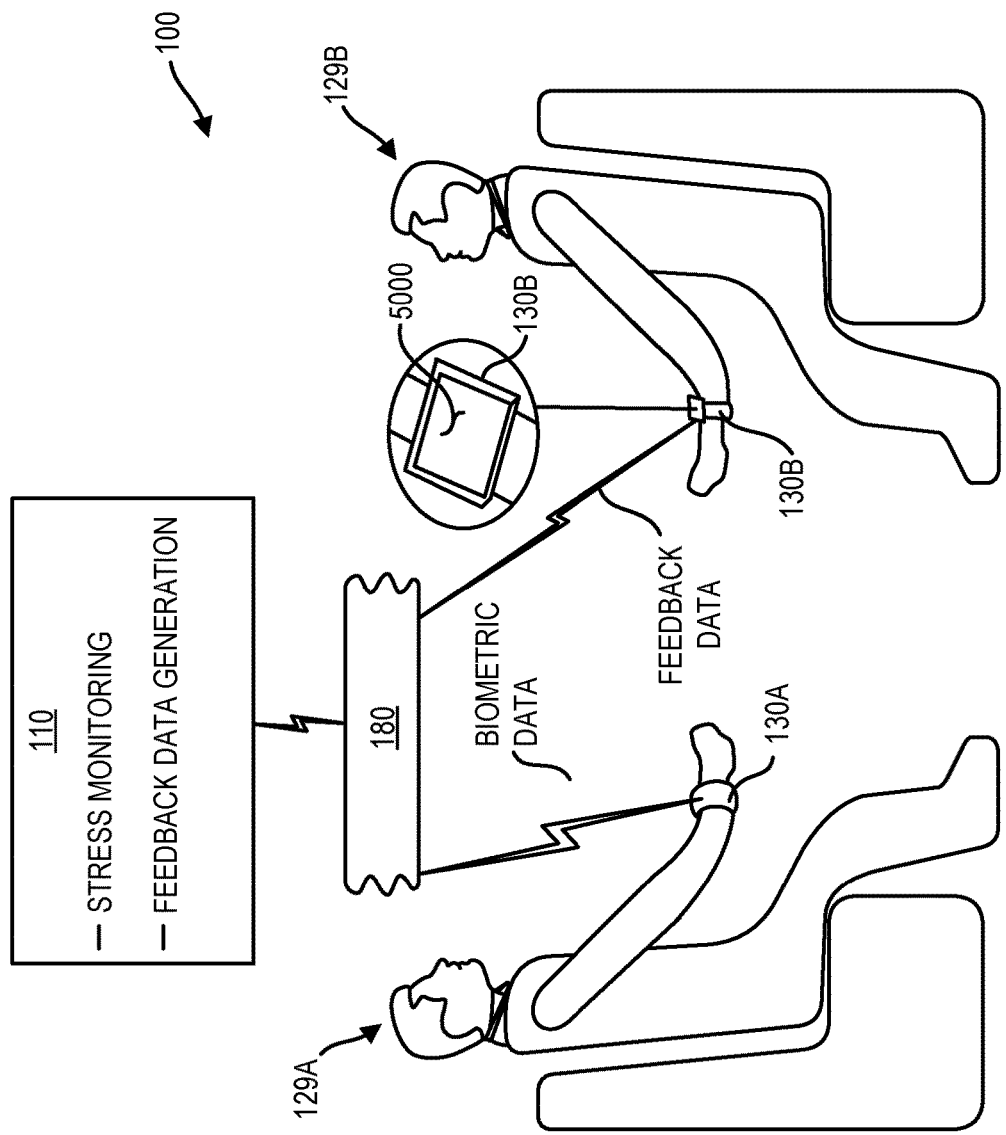
FIG. 2 is a physical schematic diagram illustrating a system as shown in FIG. 1 according to one embodiment.

FIG. 2 illustrates the physical schematic view of system 100 as set forth in FIG. 1. As depicted in FIG. 2 a first user 129A can be using a first client computer device 130A e.g. as may be provided by smartwatch or another type of mobile computer device. A second user 129B can be using a second client computer device 130B which may be provided e.g. by smartwatch or another client computer device. In the use case depicted in FIG. 2, user 129A can be a care-recipient user and user 129B can be a caregiver user. Client computer device 130A of first user 129A can send biometric data via network 180 to manager system 110 for processing by manager system 110. Biometric data can be output by one or more biometric sensor which biometric sensor can be disposed in client computer device 130A. The one or more biometric sensor can include e.g. a pulmonary sensor as set forth herein. According to another embodiment, a biometric sensor can be provided by a camera sensor which provides facial expression data of user 129A and/or an EEG sensor which provides biometric data in the form of brain activity data. An EEG sensor can be disposed in a headset worn by first user 129A. According to some embodiments a biometric sensor for output of biometric data can be an external biometric sensor disposed externally of client computer device 130A and can communicate biometric data to client computer device 130A which client computer device 130A can forward such biometric data to manager system 110 through network 180. Such an external biometer sensor can be disposed in a computing node based device that communicates with client computer device 130A via a short range e.g. BLUETOOTH® radio communication link.

Manager system 110 can activate stress monitoring process 115 to perform stress monitoring using the received biometric data and can perform feedback data generation in dependence on the stress monitoring. Manager system 110 can send generated feedback data to second client computer device 130B of user 129B who can be a caregiver user providing care to first user 129A acting as a care-recipient user. Client computer device 130B of second user 129B can provide various outputs in response to the receipt of feedback data sent by manager system 110. For example, client computer device 130B e.g. as shown in the form of a smartwatch can provide a haptic response e.g. can produce a vibration that is felt by second user 129 in response to a stress level of first user 129A. The vibration according to one embodiment can be in dependence on a classification of stress level e.g. there can be provided zero vibration for a stress level classification of "no stress," a moderate amplitude vibration for a stress level classification of "moderate stress," and a higher amplitude vibration for a high level of stress detected for first user 129A.

System 100 can be configured so that first user 129A subject to stress monitoring is unaware of second user 129B receiving any haptic response indicative of the stress level of the first user 129A. In such manner second user 129B can seamlessly respond to altering stress levels of a first user 129A without requesting first user 129A to describe his or her stress level and without first user 129A being aware that second user 129B is monitoring the first user's stress level. Second user 129B can respond seamlessly e.g. by continuing with a current course of interaction with first user 129A in the case feedback data sent to second client computer device 130B indicates no stress or alternatively in the case that feedback data indicates that the first user 129a is under stress e.g. as may be indicated by a haptic feedback e.g. a vibration. Second user 129B acting as a caregiver user can alter his or her present course of interaction with first user 129A e.g. can alter a current conversation being conducted with first user 129A so that a current conversation specifies topics that reduce the stress of first user 129A. Topics likely to reduce a stress level of first user 129A may be known by way of background knowledge known by second user 129B or, according to one embodiment, can be process-derived e.g. using machine learning processes as described herein. Topics determined to be stress reducing for first user 129A can be specified by feedback data as set forth herein sent by manager system 110 to client computer device 130B.

According to one embodiment, feedback data that is sent by manager system 110 to client computer device 130B of second user of 129B can include e.g. text or voice based prompt data that prompts second user 129B as to topics determined by processing performed by manager system 110 to be likely to reduce the stress level of first user 129A. Based on observation of such prompt data e.g. which can be textually displayed on a display of client computer device 130B or e.g. enunciated vs using an audio output device of client computer device 130B second user 129B can initiate verbal communication to first user 129A, specifying the prompted topics determined by manager system 110 to reduce the stress level of first user 129A.

FIG. 2 depicts a use case in which first user 129A and second user 129B are in a common physical environment. According to one embodiment, manager system 110 can detect a guidance session commencement when a first user and a second user 129A and 129B enter into a state to which they are in proximity e.g. within a threshold distance to one another. However, it will be understood that use cases of system 100 are not limited to a situation where a first user 129A and second user 129B are in closely spaced physical relation so that a first user 129A and second user 129B are in live verbal communication range of one another i.e. within "earshot" (within unaided live verbal communication range of one another).

According to one embodiment, first user 129A and second user 129B can be in communication with one another via a messaging system such as a messaging system of social media system 140 which messaging system can be e.g. text based, email based, and/or voice such VOIP based. Second user 129B on sensing e.g. haptic response feedback output by second client computer device 130B and/or based on output text and/or audio prompt data can alter his or her interaction with first user 129A to reduce a stress level of first user 129A.

Figure 3:
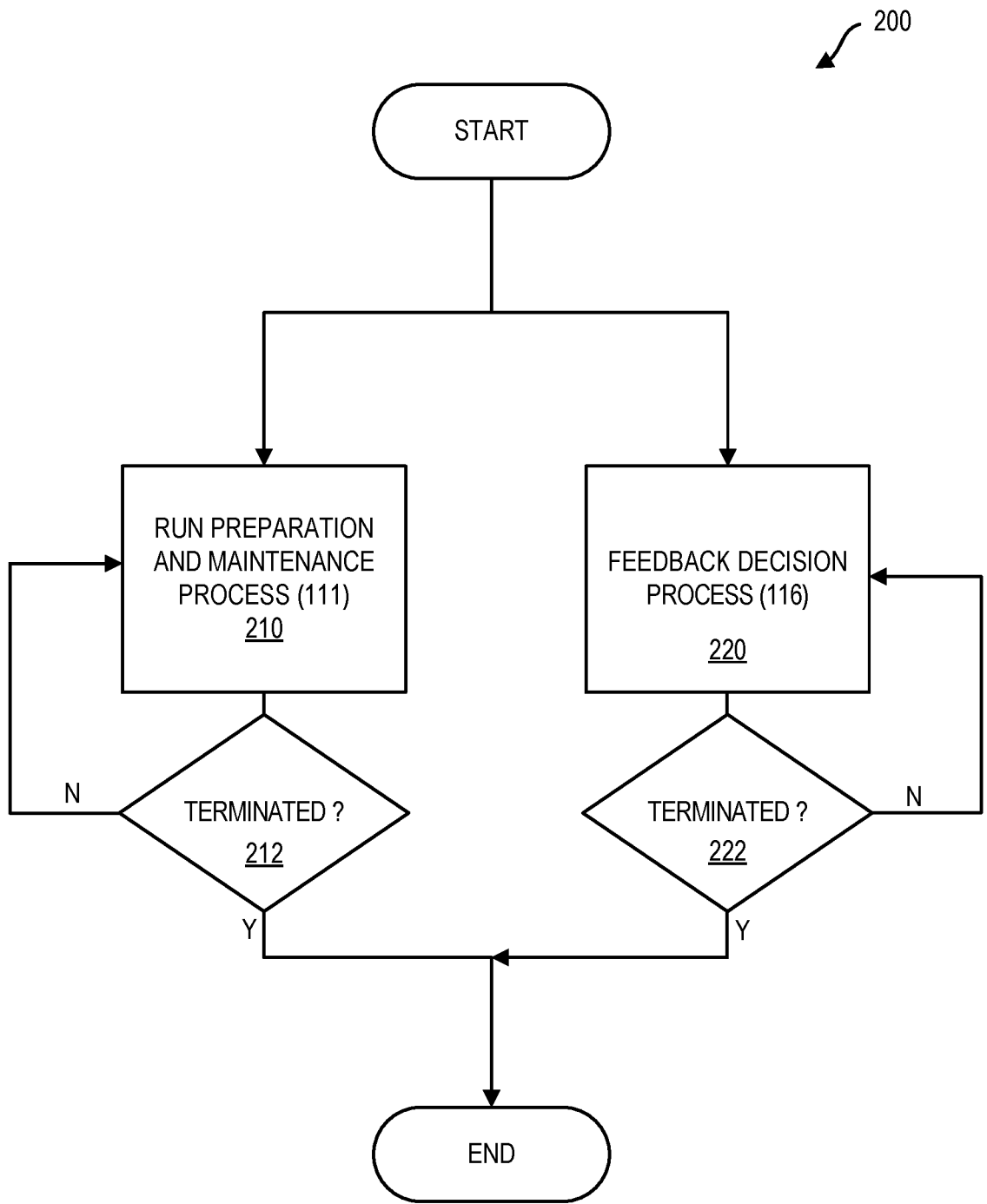
FIG. 3 is a flowchart depicting a method that can be performed by a manager system, according to one embodiment.

A method 200 for performance by manager system 110 is depicted in FIG. 3. At block 210, manager system 110 can run preparation and maintenance process 111 to populate prepare and maintain various data of data repository 112 including data of areas 2121-2124. Manager system 110 can run preparation and maintenance process 111 iteratively until process 111 is terminated at block 212. At block 220, manager system 110 can run feedback decision process 116 to return feedback data for sensing to a client computer device. For support of running of feedback decision process 116 iteratively, manager system 110 can be running e.g. NLP process 113, session detection process 114, stress monitoring process 115, feedback decision process 116 and machine learning process 117 iteratively. Manager system 110 can run feedback decision process 116 until feedback decision process 116 is terminated at block 222. Manager system 110 can run preparation and maintenance process 111 and feedback decision process 116 concurrently and can run each of process 111 and process 116 iteratively.

Figure 4A:
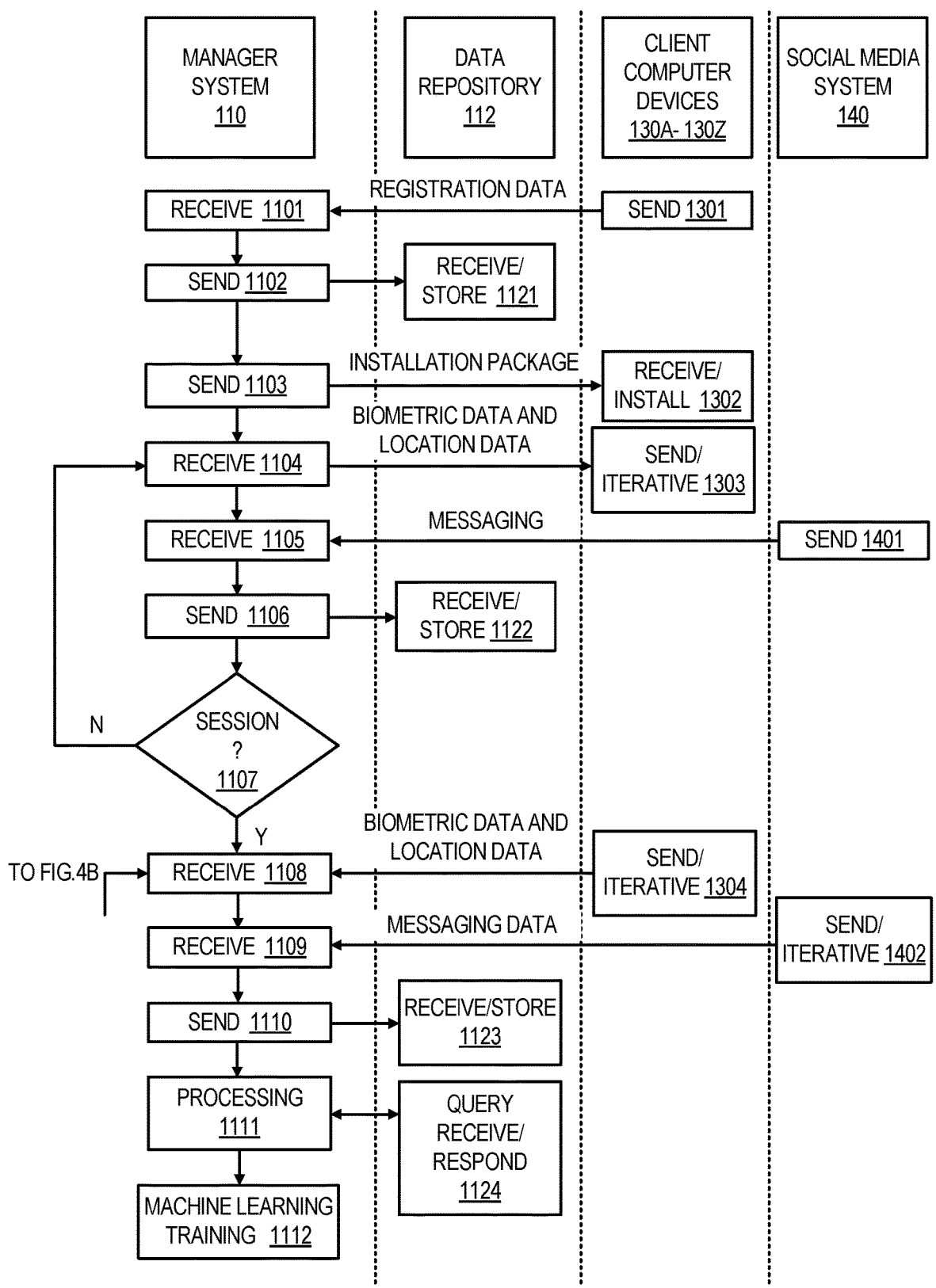
FIGS. 4A-4B is a flowchart depicting a method that can be performed by manager system interoperating with client computer devices and a social media system, according to one embodiment.
Figure 4B:
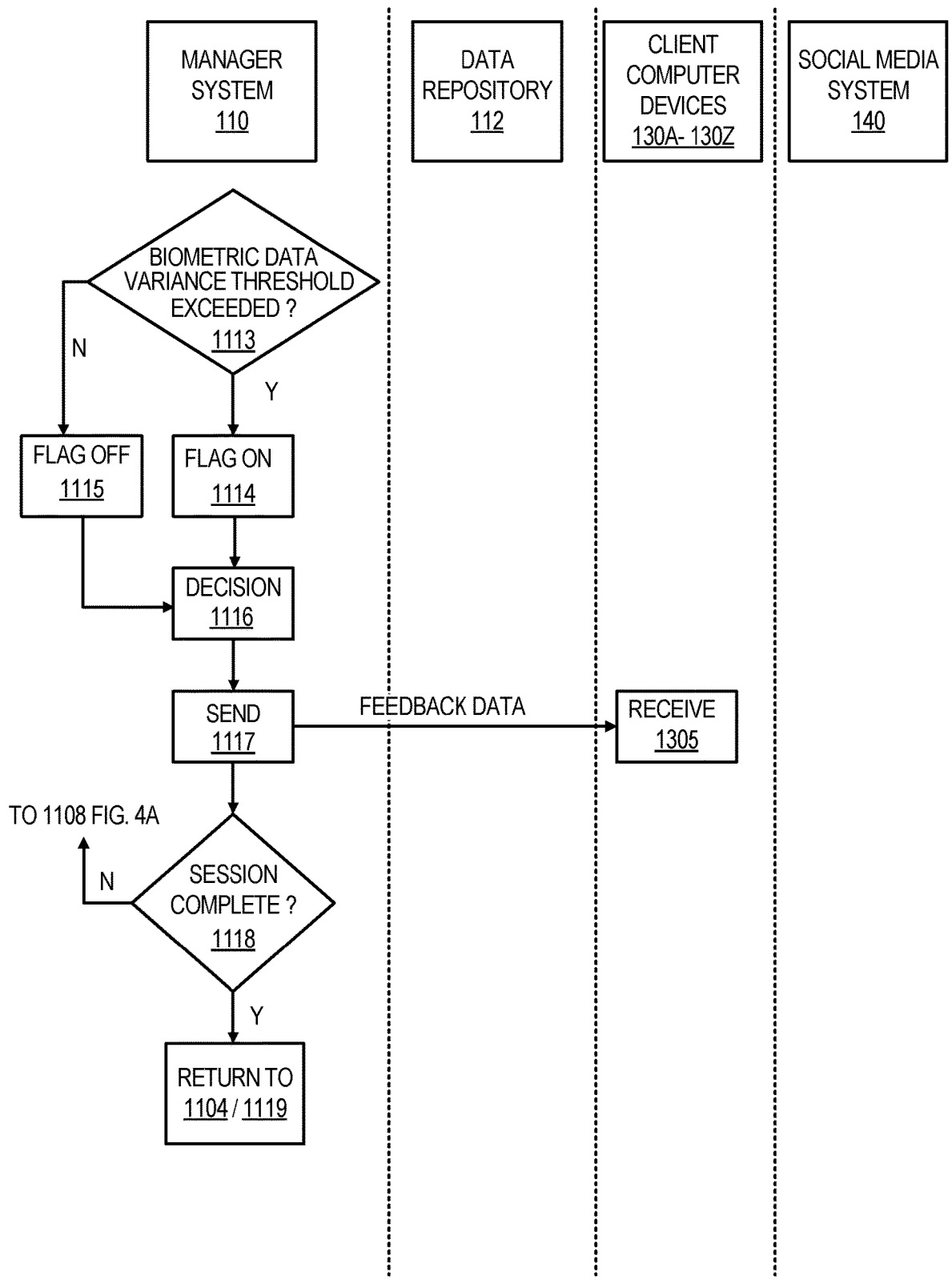

FIG. 4 is a flowchart illustrating a method for performance by manager system 110 interoperating with client computer devices 130A-130Z and social media system 140. At block 1301, client computer devices 130A-130Z can be sending registration data for receipt by manager system 110 at block 1101. In response to the receipt of registration data by manager system 110 at block 1101, manager system 110 at block 1102 sends registration to data repository 112 for receipt in storage by data repository 112 at block 1121. Users of client computer devices 130A-130Z can be entering registration data using user interface 5000 as shown in FIG. 5, wherein user interface 5000 is displayed on a display of respective client computer devices 130A-130Z.

Figure 5:
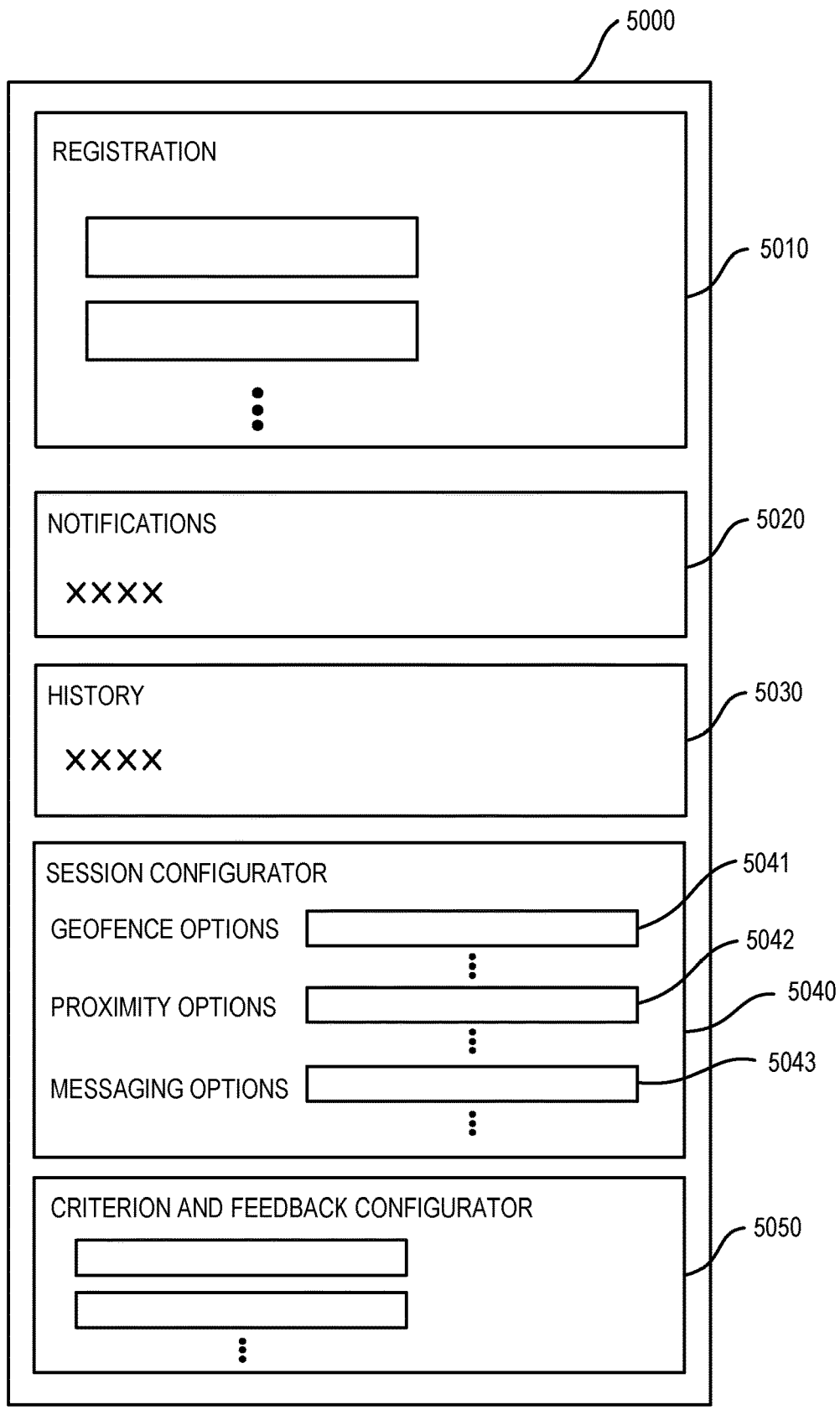
FIG. 5 depicts a user interface that can be displayed on a client computer device, according to one embodiment.

Referring to FIG. 5, a user can enter registration data using area 5010 of user interface 5000. Entered registration data can include e.g. name, address, social media account information, other contact information, biographical information, background information, preferences information, and/or permissions information e.g. can include permissions allowing manager system 110 to query data of a social media account of a user provided by social media system 140.

In response to receipt of registration data from a certain user at block 1101, manager system 110 at block 1101 can assign a UUID to each new registered user, which UUID can be stored in users area 2121 of data repository 112 at block 1121. Registration data entered by a user using user interface 5000 (FIG. 5) can include data specifying whether a registering user will be participating in system 100 as a care-recipient user, as a caregiver user, or both. Certain features of user interface 5000 can be available to a caregiver user that are not available to a care-recipient user, and vice versa.

For example, system 100 can be configured so that area 5030, 5040, and 5050 of user interface 5000 are available to a caregiver user but not available to a care-recipient user. In some embodiments area 5020 is available to a caregiver user but not available to a care-recipient user.

Manager system 110 at block 1103 can send installation packages to client computer devices 130A-130Z of registered users of system 100. In response to the sending of installation packages at block 1103, client computer devices at block 1302 can receive the installation packages and can install the installation packages on respective client computer devices 130A-130Z. Installation packages can include e.g. libraries and executable code that facilitate participation of a client computer device in system 100. A client computer device configured with software of an installed installation package can perform such functions e.g. as obtaining biometric data from a biometric sensor, integrated into client computer device 130A-130Z or external to a client computer device e.g. an EEG sensor disposed within a computing node based headset worn by a user in communication with a client computer device. Functionality provided by an installed installation package can also include such functionality as pushing biometric data obtained from a biometric sensor to manager system 110 for processing by manager system 110. Functionality provided by an installed installation package can also include e.g. outputting by a client computer device feedback to a user such as haptic feedback, visual feedback of a display screen and/or audio feedback in response to processing performed by manager system 110, the processing including processing of biometric data to return feedback data for sensing to a client computer device.

At block 1303, client computer devices 130A-130Z can be sending biometric data and location data for receipt by manager system 110 at block 1104. The biometric data can include output data of a biometric sensor e.g. a pulmonary sensor, a camera sensor sensing facial expressions, and/or an EEG sensor. Location data can include location data output by an onboard location sensor of a client computer device e.g. a GPS sensor. Location data specifying locations of client computer devices 130A-130Z for associating to biometric data can alternately be received by an alternate locating service, e.g. cellular network or wireless LAN based locating service. For providing of location data that specifies a location of users of system 100 and their respective client computer devices 130A-130Z, system 100 can be configured to provide locating services. Locating services can be e.g. control plane based, self-reported based, local range based or a combination of the noted types. In one embodiment, locating services provided by system 100 can locate a computer device of client computer devices 130A-130Z using e.g. GPS based locating services, located services based on processing of radiofrequency signals received by connection nodes of a cellular network, locating services based on processing of radiofrequency signals received by connection nodes of a wireless local area network (LAN) or a combination of such services.

Social media system 140 at block 1401 can be sending messaging data for receipt by manager system 110 at block 1105. Messaging data can include e.g. text message data, email message data, and/or voice (e.g. VOIP) data.

At block 1106, manager system 110 can send received biometric data, location data, and messaging data to data repository 112 for receipt and storage by data repository 112 at block 1122. Data stored in data repository 112 at block 1122 can be time stamped and tagged with a UUID that specifies the user associated to the stored data.

At block 1107, manager system 110 can determine whether a guidance session has been commenced. A guidance session can be a session involving first and second users having respective first and second client computer devices wherein a second user provides guidance to a first user. The first user can be a care-recipient user and the second user can be a caregiver user. In one scenario, the care-recipient user is a person receiving healthcare services and the caregiver user is a person providing healthcare services. In another scenario, the care-recipient user is a child and the caregiver user is a guardian e.g. parent guardian of the care-recipient user. In another scenario, the care-recipient user is a student and the caregiver user is a teacher.

Manager system 110 at block 1107 can activate session detection process 114 as described in connection with FIG. 1. Session detection can involve e.g. location data processing e.g. it can be determined that a session has been commenced when a first user e.g. a care-recipient user based on determined location data of a client computer device 130A (FIG. 2) of a care-recipient user has breached a geofence e.g. geofence 150 (FIG. 1). Session detection can involve e.g. location data processing e.g. it can be determined that a session has been commenced when first and second users based on determined location data of client computer devices 130A-130AZ are in proximity of one another e.g. within a threshold distance of one another.

According to another method for detecting whether a session has commenced, manager system 110 can examine messaging data as may be provided by a messaging system of social media system 140. A session can be determined to have been commenced when first and second users are in communication with one another through their respective client computer devices, using a messaging system such as a messaging system provided by social media system 140.

A caregiver user can use session configurator area 5040 of user interface 5000 to configure session commencement and/or session termination criterion. A care-recipient user can user area 5041 to specify one or more criterion based on geofence breaching. A care-recipient user can user area 5042 to specify one or more criterion based on a care-recipient user and a caregiver user being in proximity. A care-recipient user can user area 5043 to specify one or more criterion based on messaging system conversation communication between a care-recipient user and a caregiver user. When specifying a geofence 150, a user can specify geofence 150 to coincide with an area of interest, e.g. a spatial border delimiting a health care facility in which a care-recipient user may receive guidance, or spatial border delimiting a residential home in which a care-recipient user may receive guidance (e.g. in the case of a guardian relationship), spatial border delimiting a school in which a care-recipient user may receive guidance (e.g. in the case of an educational relationship).

If, at block 1107, manager system 110 determines that a session has not been commenced, manager system 110 can return to block 1104 and can iteratively perform the loop of blocks 1104-1107 until it determined that a session has been commenced. When it has been determined that a session has been commenced, manager system 110 can proceed to block 1108 and block 1109. At block 1108, manager system 110 can be receiving biometric data and location data. At block 1304 client computer devices 130A-130Z can be sending biometric data and location data for receipt by manager system 110 at block 1108. Manager system 110 can alternatively receive location data associated to a client computer device from alternative device locating service. Social media system 140 at block 1402 can be sending messaging data for receipt by manager system 110 at block 1109.

At block 1110, manager system 110 can send received biometric data and location data (received at block 1108) and received messaging data (received at block 1109) to data repository 112 for receipt and storage by data repository 112 at block 1123. Biometric data and location data sent at block 1304 can be biometric data and location data of first and second users participating in a session identified at block 1107. Messaging data sent at block 1402 can be communication messaging data of communication messages between the first and second session participant users of the session identified at block 1107.

Received data received by manager system 110 at block 1108 and 1109 can be time stamped data e.g. time stamped by client computer devices 130A-130Z, social media system 140 and/or manager system 110.

Manager system 110 at block 1111 can activate stress monitoring process 115. Manager system 110 at block 1111 can perform processing of received biometric data and location data received at block 1108 and processing a received messaging data at block 1109. Processing at block 1111 can include multiple queries of data repository 112 as indicated by query receive and respond block 1124, performed by data repository 112. Processing performed by manager system 110 at block 1111 can include processing to return biometric variance values in dependence on biometric data. Biometric variance values returned by manager system 110, at any given point in time can specify a difference between a current value for a biometric data parameter and a baseline biometric data parameter value which baseline biometric data parameter for a certain user can be returned by querying of data repository 112.

Manager system 110 performing processing at block 1111 can include manager system 110 activating NLP process 113 to process text-based and/or voice based messaging data received at block 1109. Manager system 110 can subject received text-based and or voice-based messaging data to NLP processing to return topic classifications of a current text based and/or voice based conversation between a care-recipient user and a caregiver user, during a current session. For processing of voice based messaging data, manager system 110 can activate a speech to text converter and then can process the returned text. Speech to text serviced provided by IBM® WATSON® speech to text services can be utilized (IBM® and WATSON® are registered trademarks of International Business Machines Corporation). Manager system 110 can send updated data values returned at block 1111 for storage into data repository 112 at block 1124. Returned data values can include, for example, returned biometric variance data values, stress classification data values and returned topic classifications returned by activation of NLP process 113 to subject received messaging data. At block 1111 manager system 110 can process received biometric data to return stress level classification data for a user. Manager system 110 can activate stress monitoring process 115 to monitor and process biometric data received from client computer devices 130A-130Z for respective users of the client computer devices 130A-130Z and can process the received biometric data to return biometric variance data. For return of biometric variance data, manager system 110 can process received biometric data for establishing and maintaining biometric baseline data for each user, e.g. based on an average of biometric data parameter values over time. Manager system 110 can return a biometrics variance value for a user based on a difference between a current biometric data parameter value and a baseline biometric data parameter value for a given biometric parameter. In dependence on returned biometric variance data values, manager system 110 can return stress level classifications. According to one embodiment, manager system 110 running stress monitoring process 115 (FIG. 1) can return a stress level within one of two stress level classifications e.g. a stressed classification and un-stressed classification, where a stress level classification is determined based on biometric variance data values exceeding a stress indicating threshold. Manager system 110, according to some embodiments, can return multiple stress level classifications e.g. according to one embodiment, two classification levels of stress, e.g. "stressed" and "not stressed" or, in one embodiment, three classification levels of stress e.g. "highly stressed," "stressed," or "not stressed," wherein the various stress level classifications are all in dependence on a return current variance value exceeding a threshold value. In one embodiment, manager system 110 can provide an N stress level classification system where N>3 in dependence on biometric variance data values exceeding defined thresholds.

Manager system 110 at block 1111 can be sending updated data values, e.g. biometric variance values, stress level classification values, and/or topic classification values returned from processing messaging data for storage by data repository at block 1124. Data repository 112 accordingly can store for each user historical timestamped values that specify a history of each user's biometric variance values and stress level classifications over time associated to conversation text and returned topics returned by processing of the text at each specified time segment. A caregiver user can use area 5030 of user interface 5000 (FIG. 5) to view the historical data at any time. A caregiver user using area 5030 can look up a care-recipient user's recent stress history to highlight in area 5030 with text time segments in which the user experiences the highest stress. Simultaneously with the stress level indicating text there can be displayed text specifying words and/or returned topics of the words associated to stress classifications indicated in area by having common timestamps of the indicated stress classification. A caregiver user thus is informed as to conversation words and/or topics to avoid in order to reduce an exhibited stress level of the care-recipient user. There is set forth herein according to one embodiment a method, wherein the method includes displaying on a displayed user interface 5000 displayed on the second client computer device 130B of a caregiver user 129B (FIG. 2) historical data of the first user 129A (FIG. 2), wherein the displayed historical data includes for a certain historical time segment, text specifying a stress level classification of the first user during the certain historical time segment associated to text specifying words of a conversation between the first user and the second user during the certain historical time segment, wherein the user interface 5000 permits the second user to view data of historical time segments sorted on the basis of exhibited stress level of the first user that is associated to the time segment, and wherein the displayed historical data for the certain historical time segment is displayed on the displayed user interface 5000 in response to a search entered by the second user into the user interface 5000 for data of historical time segments in which the first user exhibited a stress level specified by a data entry of the second user 129B (FIG. 2) into the user interface 5000.

Figure 6:
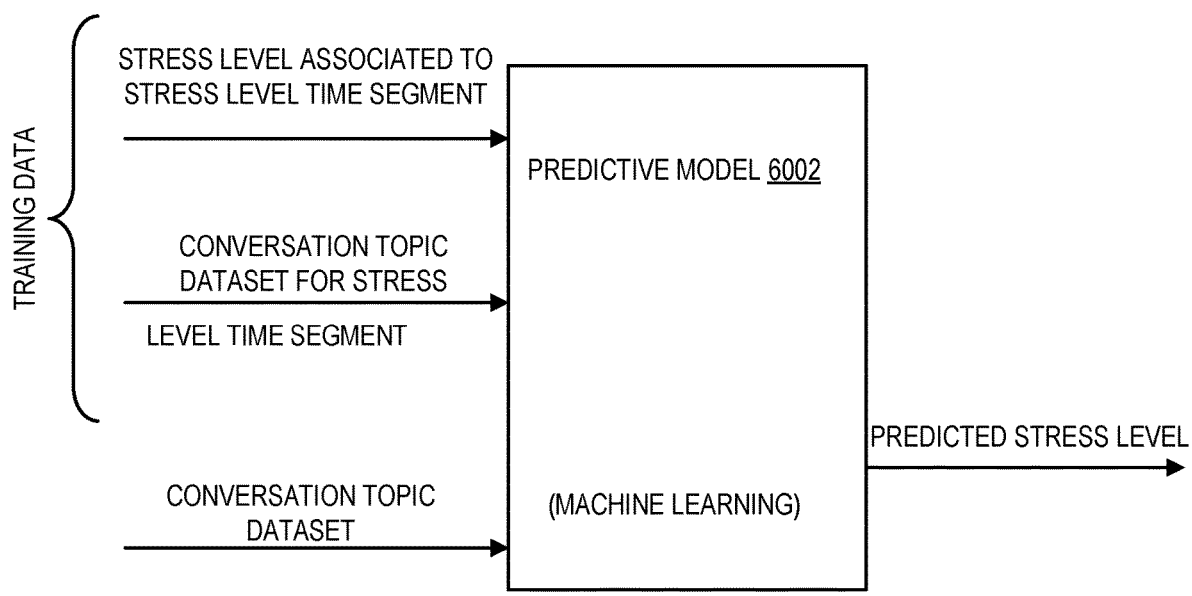
FIG. 6 depicts predictive model that can be trained by machine learning, according to one embodiment.

Manager system 110 on completion at block 1111 can proceed to 1112. At block 1112, manager system 110 can perform machine learning training of predictive model 6002 as shown in FIG. 6. Predictive model 6002 as shown in FIG.

6, once trained by machine learning, can respond and predict stress level of a user in response to query data specifying a prospective one or more conversation topic. Various candidate topics can be input as query data to a predictive model 6002 and predictive model 6002 can return a predicted stress level associated with each topic.

At block 1112, manager system 110 can apply an iteration of training data to a predictive model 6002, so that training of predictive model 6002 is updated to facilitate predictive model being able to respond to query data specifying one or more conversation topics. Predictive model 6002 can be trained by way of supervised machine learning. There can be applied to predictive model 6002 training data. Training predictive model 6002 at block 1112 can include applying to predictive model 6002 training data that comprises a stress level classification for a user associated to a stress level time segment, in combination with a topic data set for the certain stress level time segment. By application of the described training data which can be iteratively applied, predictive model 6002 can learn topics which can increase stress to a user and which topics can reduce a user's stress. Over the course of deployment of manager system 110, when a session is active, manager system 110 can be associating a stress level classification for a care-recipient user to returned topic classifications of a current conversation, participated in by the care-recipient user e.g. topics of voice messages, of text based and/or voice based messaged presented to the care-recipient user by a caregiver user during a guided session.

The stress level data associated to topic classification data can be timestamped. Manager system 110 can divide timestamped data into time segments referred to as stress level time segments, that are divided by transition periods defined by a stress level classification changing (e.g. from unstressed to stressed). A time segment can be terminated, and a next time segment commenced on the transition of a stress level between stress level classification e.g. between the classifications of "not stressed" to "stressed" or between the stress level classifications of "stressed" to "highly stressed." The methodology can be adapted to the particular stress level classification system utilized (e.g. 2 level, 3 level N level). At block 1112, manager system 110 can apply to predictive model 6002 training data (e.g. comprising stress level classification data and topic data) for the most recently identified stress level time segment of a care-recipient user.

Various available tools, libraries, and/or services can be utilized for implementation of predictive model 6002. For example, a machine learning service can provide access to libraries and executable code for support of machine learning functions. A machine learning service can provide access set of REST APIs that can be called from any programming language and that permit the integration of predictive analytics into any application. Enabled REST APIs can provide e.g. retrieval of metadata for a given predictive model, deployment of models and management of deployed models, online deployment, scoring, batch deployment, stream deployment, monitoring and retraining deployed models.

Manager system 110 at block 1113 can determine whether a biometric variance threshold is exceeded. As stress level classifications can vary in dependence on biometric variance data, manager system 110 at block 1113 can examine a current stress level classification of a care-recipient user. According to one embodiment, manager system 110 at block 1113 can determine whether a current care-recipient user is currently under stress (e.g. has a stress level classification at least of "stressed") and can examine a stress level classification. In response to determination that a biometric variance threshold is exceeded at block 1113, manager system 110 at block 1114 can raise a haptic flag. When a haptic flag is raised, manager system 110 is operative to send haptic response feedback data to a caregiver user. In response to a determination at block 1113 that a current biometric variance for a care-recipient user has not exceeded a threshold, manager system 110 at block 1115 can turn off a haptic flag.

Manager system 110 at block 1116 can activate feedback decision process 116 to return a decision as to feedback data to send to participant users of a current guidance session feedback data sent to client computer devices can include e.g. haptic response feedback data and/or prompt feedback data. Haptic response feedback data can include data which when received by a receiving client computer device results in the client computer device providing haptic feedback to a participant user such as a caregiver user according to one embodiment, haptic response can result in a vibration output provided by a client computer device which varies in dependence on a current stress level of a care-recipient user e.g. a relatively smaller magnitude of vibration for a lower stress level classification and a stronger level of vibration when a care-recipient user is currently exhibiting a higher stress level classification.

Haptic feedback provided to a caregiver user can provide various advantages. For example, such a response can be provided in a manner so that a care-recipient user is unaware that the caregiver user is monitoring the care-recipient users stress level. Such functionality can enhance the caregiver user's ability to respond productively to the care-recipient users stress, increasing the likelihood that the caregiver user can interact with the care-recipient user in a manner to reduce stress. Based on haptic feedback being provided to a caregiver user, the caregiver user can react in real time in a manner to reduce the care-recipient's stress. For example, can take action to change conditions of a current environment, including topics currently being discussed in a conversation between a caregiver user and a care-recipient user. A caregiver user on receipt of haptic response feedback from a client computer device used by the caregiver user can change a current topic of verbal conversation with a care-recipient user to a new topic. The new topic can be specified in a prompt presented to the caregiver user by manager system 110 by the sending of feedback data or the new topic may not be specified in any feedback data. Embodiments herein recognize that a user's health can be in dependence on a stress level. Accordingly, embodiments herein can improve the health and wellbeing of participant care-recipient users.

Feedback data provided to a client computer device or sent to a client computer device can include such data as text data and/or voice data that defines a prompt for prompting a caregiver user. Prompting data defined by text data for example can be displayed in notifications area 5020 of user interface 5000 as shown in FIG. 5. Prompt data can include text-based data e.g. as displayed in area 5020 and/or voice prompt data output by an audio output device of a client computer device.

Prompt data can include data that advises users of conditions of interest in an environment in which a care-recipient user is located. For example, according to one embodiment, manager system 110 at block 1111 can be examining stress level data associated with location data of a current care-recipient user, as specified in stress history area 2122 of data repository 112. Based on such data examining, manager system 110 can determine that the care-recipient user, has entered into an area in which, based on the examination of historical data, the care-recipient has historically exhibited a high level of stress.

Accordingly, based on such examining, manager system 110 at block 1116 can return the feedback data decision to send text based and/or voice prompt feedback data advising a caregiver user and/or care-recipient user that the care-recipient user is currently in an area (e.g. a doctor's office or a pharmacy) where the caregiver user historically exhibits stress. Accordingly, the users' can have knowledge that a level of stress, currently being exhibited by a character recipient user, is a result of the current location of the user and in such a situation, a caregiver user and/or care-recipient user can initiate activity to change a current location of the care-recipient user.

Manager system 110 at decision block 1116 can query predictive model 6002 to return useful prompt feedback data. According to one embodiment, manager system 110 at block 1116 can input a set of candidate topics as query data to predictive model 6002 as described in connection with FIG. 6. The candidate topics can be topics of a predefined list, according to one embodiment, or can be adaptively derived based on returned topic classifications of a current conversation.

Manager system 110 at block 1116 can apply as query data to predictive model 6002 various candidate topic classifications and can examine returned predicted stress levels associated with each of the candidate topics. Manager system 110 can select one or more selected topics from the candidate list of topics in dependence on which of the one or more candidate topics produces the lowest predicted level of stress in response to a query of predictive model 6002.

Manager system 110 at block 1116 can specify the selected lowest stress reducing topics for sending to a user in feedback data sent to a client computer device. According to one specific embodiment, a care-recipient user can be a healthcare services recipient e.g. a patient and a caregiver user can be a healthcare services provider e.g. a physician.

A healthcare treatment plan can be divided into various stages and system 100 can be used to present a treatment plan in a manner to reduce the least amount of stress in the care-recipient user. A healthcare treatment plan can be divided e.g. into various stages such as the stages of pre-treatment options, treatment options, and post-treatment options each with a plurality of different options. Prior system 100 can be configured so that manager system 110 determines for each stage, the least stressful options. For each stage, by query of predictive model 6002, and specifies the option, determined with use of predictive model 6002, to be the least stress-inducing. For example, treatment options for a particular treatment plan can include the options of "taking pills," or "applying shots," or "surgery." Manager system 110 can present prompt data to a caregiver user so that the option determined likely to induce the least amount of stress in a care-recipient user is presented. The least stress-inducing option can be determined by querying of predictive model 6002 as set forth herein. Prompt options can be presented with text in notifications area 5020 of user interface 5000 and/or can be presented with an audio output by activation of an audio output device of a client computer device used by a caregiver user to the caregiver user e.g. through an earpiece worn by a caregiver user.

Manager system 110 can use a decision data structure of decision data structures area 2124 at block 1116. An example of a decision data structure is shown in Table A.

TABLE A

| Row | Care-Recipient User's Stress level classification | Feedback data Action Decision |
|---|---|---|
| 1 | Unstressed | Text-based only |
| 2 | Stressed | Text based data and haptic feedback control data to control vibrations of vibration producing output device of a caregiver user's client computer device to vibration amplitude 1. |
| 3 | Highly stressed | Text based data and haptic feedback control data to control vibrations of vibration producing output device of a caregiver user's client computer device to vibration amplitude 2, 2 > 1. |

Table A depicts a decision data structure for return of haptic feedback data in dependence on stress level classification. For a stress level classification of a care-recipient of "unstressed," feedback data can be absent of haptic feedback data (a caregiver user will not feel any vibration). For a stress level classification of "stressed" a caregiver user will feel a vibration of amplitude 1. For a stress level classification of "highlight stressed" a caregiver user will feel a vibration of amplitude 2, 2>1. Referring to Table A haptic feedback data can alternatively be provided to specify a count of vibration events in dependence on a stress level classification, e.g. no vibration event in the case of an unstressed stress classification, a single vibration event in the case of a stress classification of stressed, and two closely time spaced vibration events in the case there is returned a stress level classification of "highly stressed". System 100 can be configured so that feedback it iteratively presented to a caregiver user for as long as a stress level classification persists.

Manager system 110 at block 1119 can send feedback data for receipt by a caregiver user's client computer device and/or a care-recipient's client computer device at block 1305. In response to the received feedback data at block 1305, the client computer device receiving the feedback data outputs a feedback to a user e.g. haptic feedback or non-haptic feedback provided e.g. by text based feedback and/or voice based feedback. A caregiver user can use area 5050 of user interface 5000 to configure criterion resulting in feedback data being sent to a client computer device of a caregiver user, and/or to configure the feedback data.

At block 1118, manager system 110 can determine whether a current guidance session has been completed. Manager system 110 at block 1118 can determine that a current guidance session is terminated e.g. when a first user e.g. care-recipient user having client computer device 130A (FIG. 2) has exited a geofence. Manager system 110 at block 1118 can determine that a current guidance session is terminated e.g. when first and second users have separated from one another and are now located at greater than a threshold distance from one another.

Manager system 110 at block 1118 can also determine that current guidance session has been terminated by monitoring of a messaging system of social media system 140 to determine that a current conversation has terminated. Manager system 110 at block 1119 can return to block 1104. In response to determination that a current guidance session is not completed at block 1118. Manager system can return to block 1108 and can iteratively perform block 1108-1118 iteratively until a current session has been completed.

Embodiments herein recognize that certain scenarios and interactions may have a significant effect on a person's stress level as can be indicated by heart rate and other vitals. Embodiments herein recognize that at times it can be advantageous for a second person to be aware of the increased stress without the original person being aware of the monitoring.

Embodiments herein provide for a responsible party, like a doctor or other health care provider, parent, a spouse, to monitor the health of a care-recipient without having to intervene or intrude their natural actions or environments.

Figure 7:
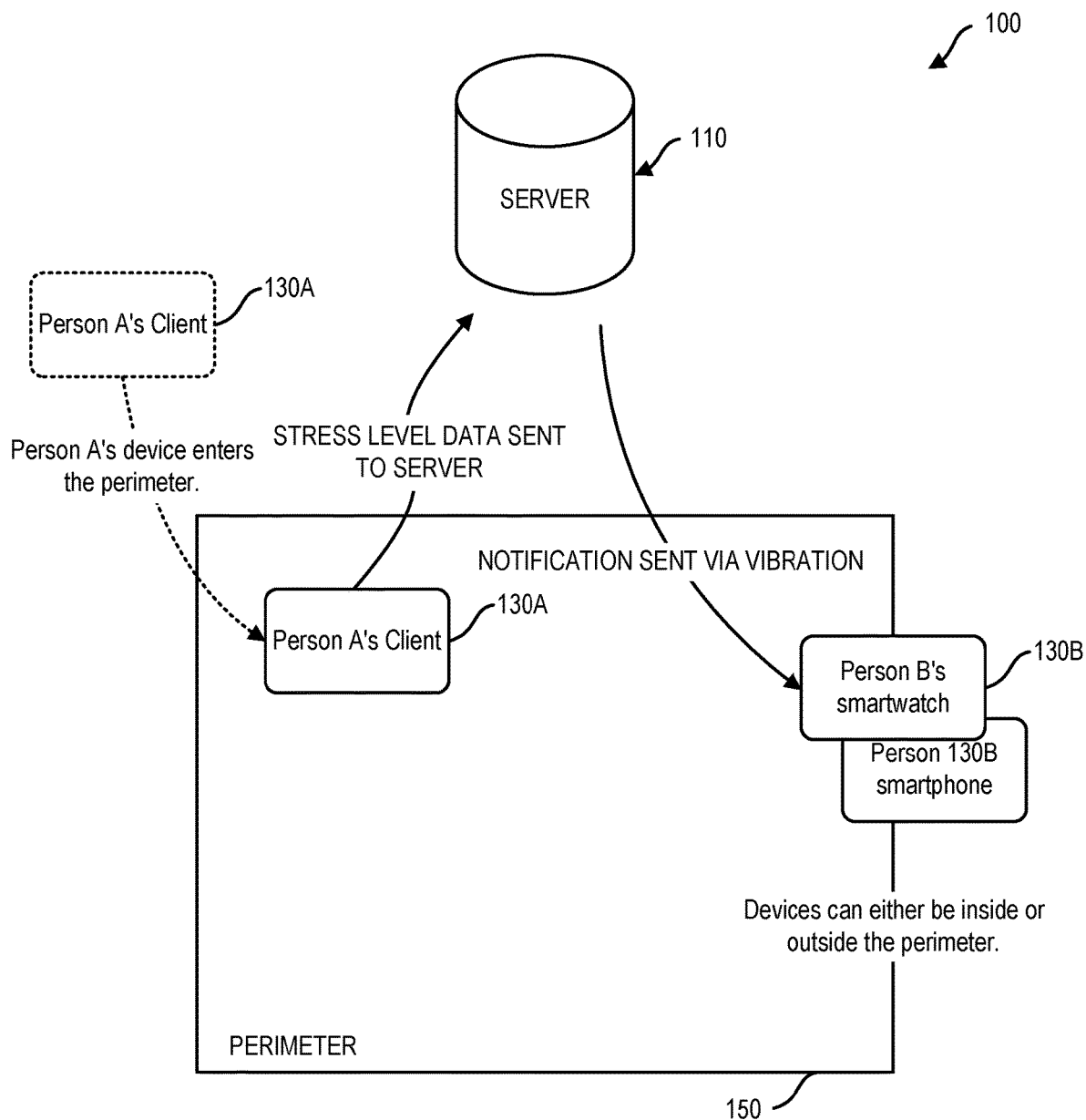
FIG. 7 depicts a system for reduction of stress level of a user.

A further example of system 100 as set forth in FIGS. 1 and 2 is set forth in FIG. 7. System 100 is set up to monitor the stress level of an individual based on interpretation of data provided by one or more biometric sensor which can be disposed internally or externally of a client computer device 130A of a care-recipient user A. System 100 allows for a second person B (a caregiver user) to be notified of indications of increased stress through a mobile device that will provide haptic feedback so the original person A (care-recipient user) is not aware of the information sharing. In addition, system 100 can save the data feeds and compare them over time to similar scenarios to see if stress levels are increasing or decreasing in those scenarios and provide that feedback via a similar process which allows for sharing the different feeds (e.g. vibration amplitude 1, v. vibration amplitude 2, single vibration v. double vibration).

System 100 can be configured so that an interested party, Person B (caregiver user), can monitor the stress and discomfort levels of Person A (care-recipient user), real time with unobtrusive using haptic feedback alerts in a predefined perimeter. According to one specific implementation the following can occur: (1) A doctor (Person B) can be talking to a patient (Person A); (2) the system 100 can determine that the patient is very nervous; (3) the doctor's watch responsively vibrates responsively to the determination that the patient is nervous; (4) in response to the haptic feedback the doctor talks to the patient specifying an alternative treatment method.

System 100 as shown in FIG. 7 can include Person B, a Party who views data, client computer device 130B, a mobile/wearable device associated with Person B. System 100 can include Person A, a party whose data is recorded, client computer device 130A, a mobile/wearable device associate with Person B. System 100 can include a manager system 110 having a server—a system which receives and stores data, a sends feedback data to client computer device 130B of Person B.

Manager system 110 (including a "Server") can be set up to communicate with an array of client computer devices including client computer device 130A and client computer device 130B. One or more biometric sensor (e.g. a pulmonary, camera or EEG sensor) disposed internally or externally of client computer device 130A can output biometric data associated to Person A.

Person B can configure the manager system 110 having a server with a geolocated geofence 150 defining a location where Person A will be tracked, e.g. an area within which biometric data associated to Person A can be processed for return of stress level classification for Person A. Stress level classification can be returned based on an output of one or more biometric sensor.

Person B can configure how they would like to receive feedback from manager system 110 having a server (different vibration amplitudes and/or patterns, text and/or sound notification, etc.)

Person A can install the tracking software on client computer device 130A, the mobile and wearable devices.

When Person A breaches the defined geofence 150, client computer device 130A of Person A automatically begins tracking data regarding for return of stress level classification, without any notification or distraction.

Biometric data output by a biometric sensor can be encrypted and sent to the manager system 110 having a server. Manager system 110 can examine the data looking for anomalies, spikes, and trends regarding Person A's health.

If manager system 110 finds any alerts, feedback data can be sent to client computer device 130A of Person B (mobile, wearable, etc.) so that client computer device 130B produces subtle feedback in dependence on a stress level classification of Person A.

Person B can receive feedback from the Server depending on how they have configured their alerts. The intensity of the haptic response being presented to Person B can be proportional to the stress level being exhibited by Person A. Over time, system 100 can become more accurate through machine learning, offering Person B with differentiated responses are personalized to Person A and the pertaining situation.

Figure 8:
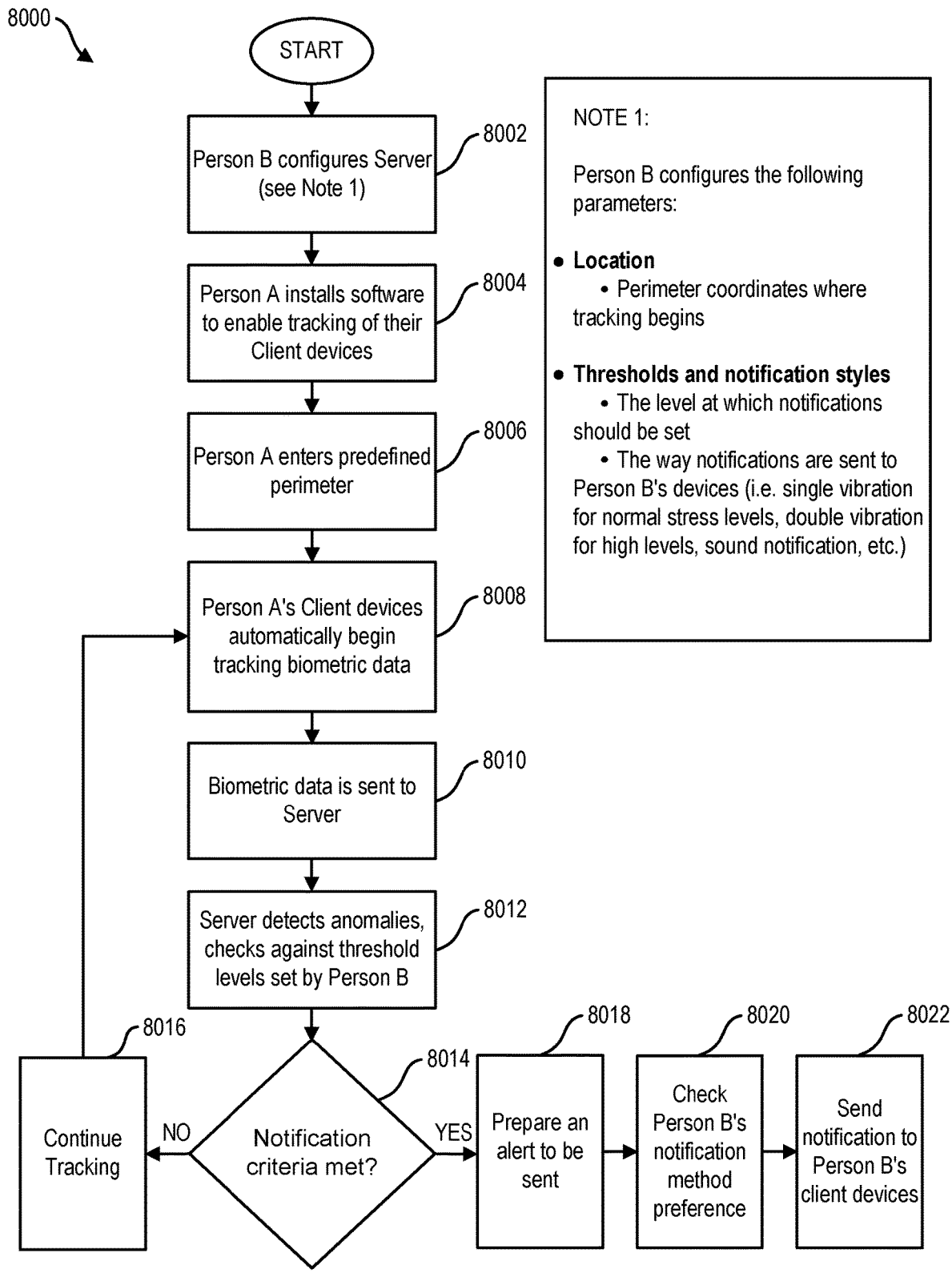
FIG. 8 is a flowchart for performance by a system for reduction of stress level of user.

FIG. 8 is a flowchart depicting operation of system 100 according to one embodiment. At block 8001 Person B can configure a server defining manager system 110. At block 8004, person A can install software in their client computer device 130A to enable tracking. At block 8006 Person A can enter geofence 150. At block 8008 client computer device 130A automatically commences obtaining of biometric data for use in determination of stress level. At block 8010 biometric data can be sent to manager system 110. At block 8012 manager system 110 can process the biometric data for return of stress level classification. At block 8014 manager system 110 can determine if a notification criterion is satisfied. If a notification criterion is not satisfied, tracking can continue (block 8016). If a notification criterion is satisfied, manager system 110 can prepare an alert to be sent (block 8018), check Person B's notification preference (block 8020) and send a notification for display on a display of client computer device 130B e.g. for display in notification area 5020.

Certain embodiments herein may offer various technical computing advantages involving computing advantages to address problems arising in the realm of computer system and computer networks, particularly, computer system and networks operating to provide location based services (LBS). Embodiments herein can provide enhanced user interface functionality so that actions of a first user can be automatically sensed by a second user and, further, so that inputs can be provided by a computer system without manual input on behalf of the user and a computer system can react in a way to benefit the users absent of traditional user interface data entry processes. Embodiments herein can improve the health and welfare of users and can reduce risk situations by reduction of stress levels of users in dependence on interactions with users by other users. Embodiments herein have features so that caregiver users interacting with care-recipient users can interact with care-recipient users in a manner to reduce stress to therefore improve risk situations. Artificial intelligence (AI) processes can be employed; for example, to process biometric data for return of biometric data and stress level classification. Processes can be employed to convert speech to text and Natural Language Processing (NLP) can be employed to convert speech to topic classifications, which topic classification can be applied for training of a predictive model trained by supervised machine learning processes. Various decision data structures can be used to drive artificial intelligence (AI) decision making, such as decision data structure that cognitively maps stress levels to haptic feedback selections. Decision data structures as set forth herein can be updated by machine learning so that accuracy and reliability is iteratively improved over time without resource consuming rules intensive processing. Machine learning processes can be performed for increased accuracy and for reduction of reliance on rules based criteria and thus reduced computational overhead. For enhancement of computational accuracies, embodiments can feature computational platforms existing only in the realm of computer networks such as artificial intelligence platforms, and machine learning platforms. Embodiments herein can employ data structuring processes, e.g. processing for transforming unstructured data into a form optimized for computerized processing. Embodiments herein can examine data from diverse data sources such as data sources that process radio signals for location determination of users. Embodiments herein can include artificial intelligence processing platforms featuring improved processes to transform unstructured data into structured form permitting computer based analytics and decision making. Embodiments herein can include particular arrangements for both collecting rich data into a data repository and additional particular arrangements for updating such data and for use of that data to drive artificial intelligence decision making.

Figure 9:
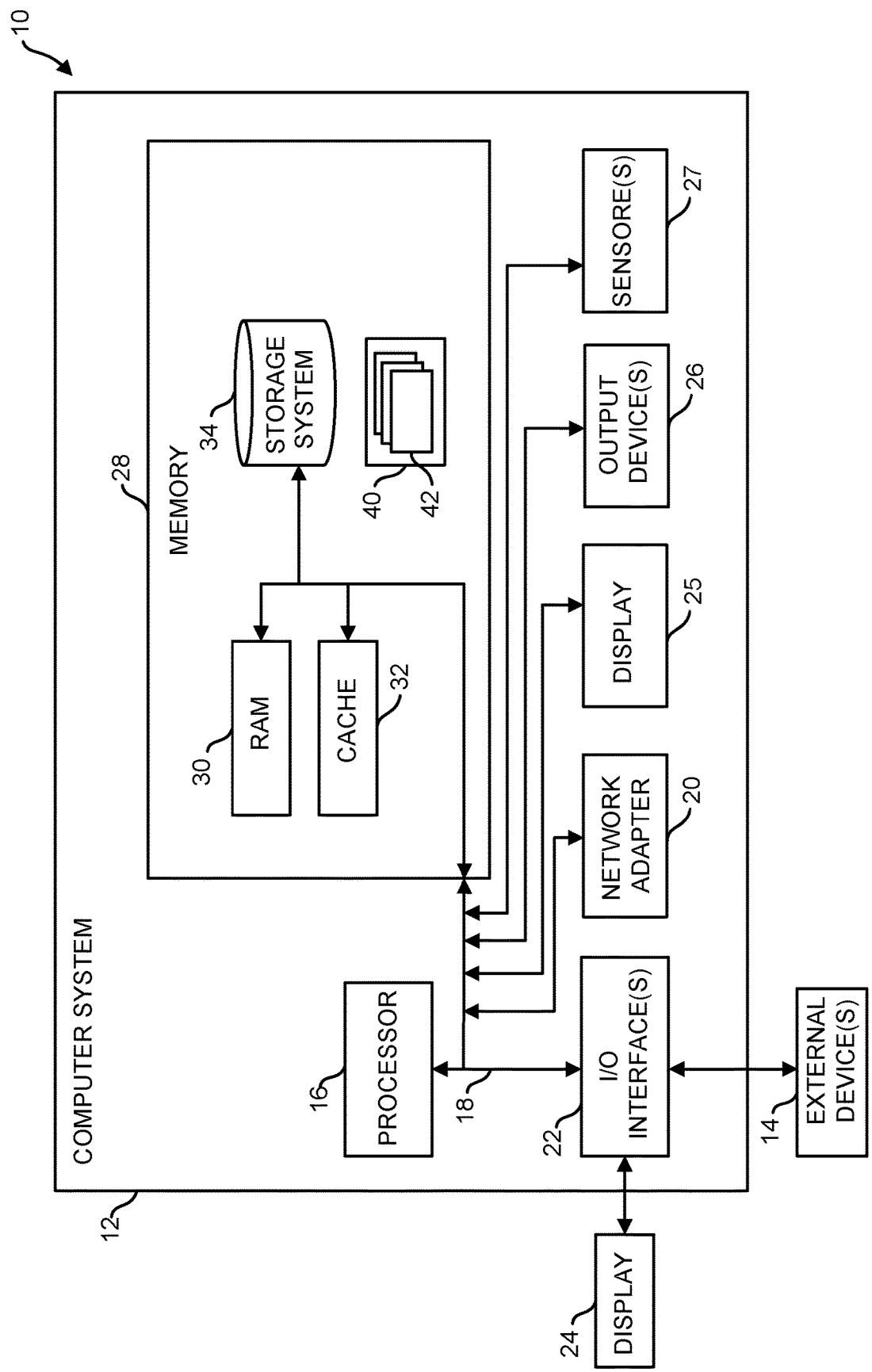
FIG. 9 depicts a computing node according to one embodiment.
Figure 10:
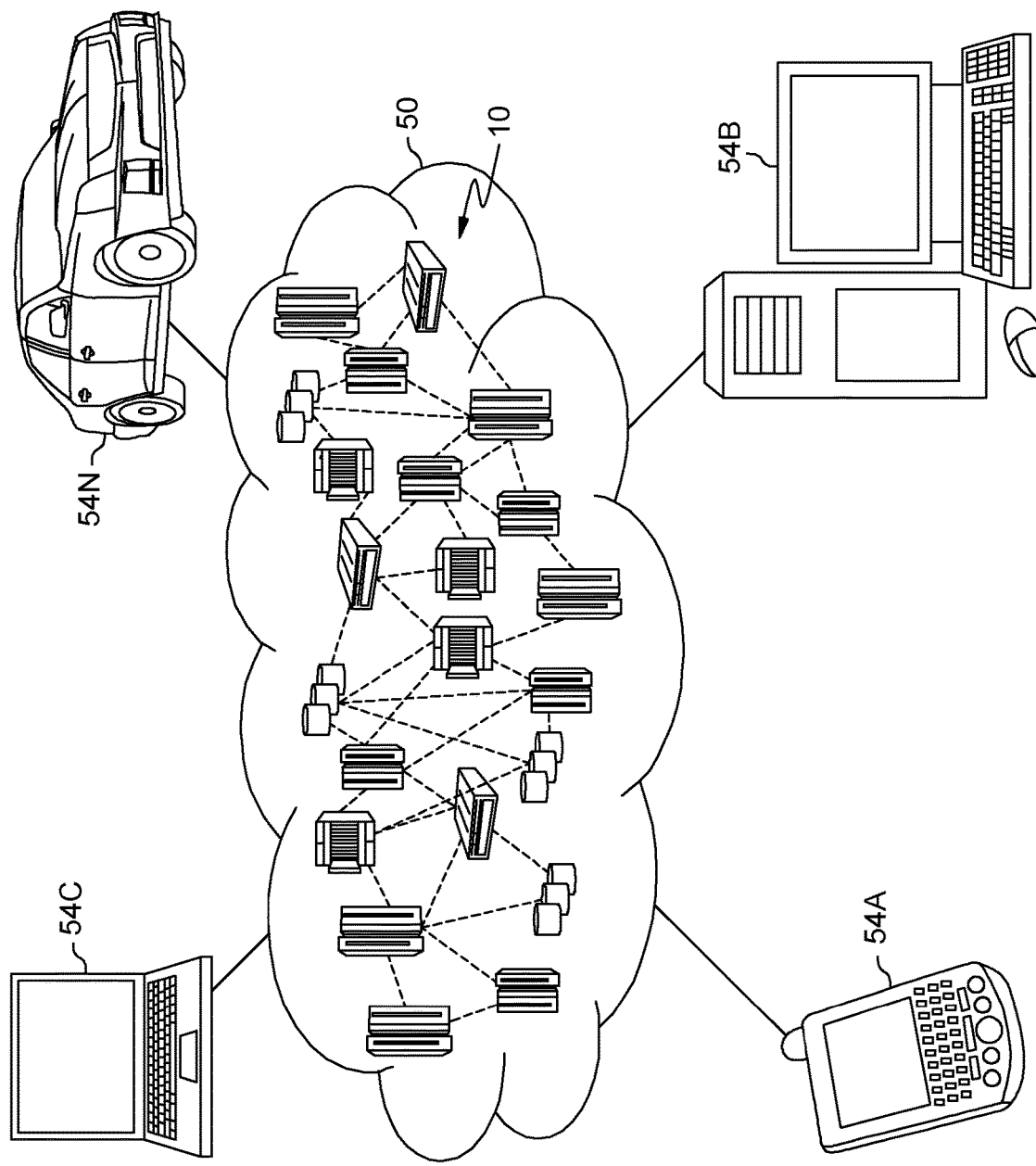
FIG. 10 depicts a cloud computing environment according to one embodiment.
Figure 11:
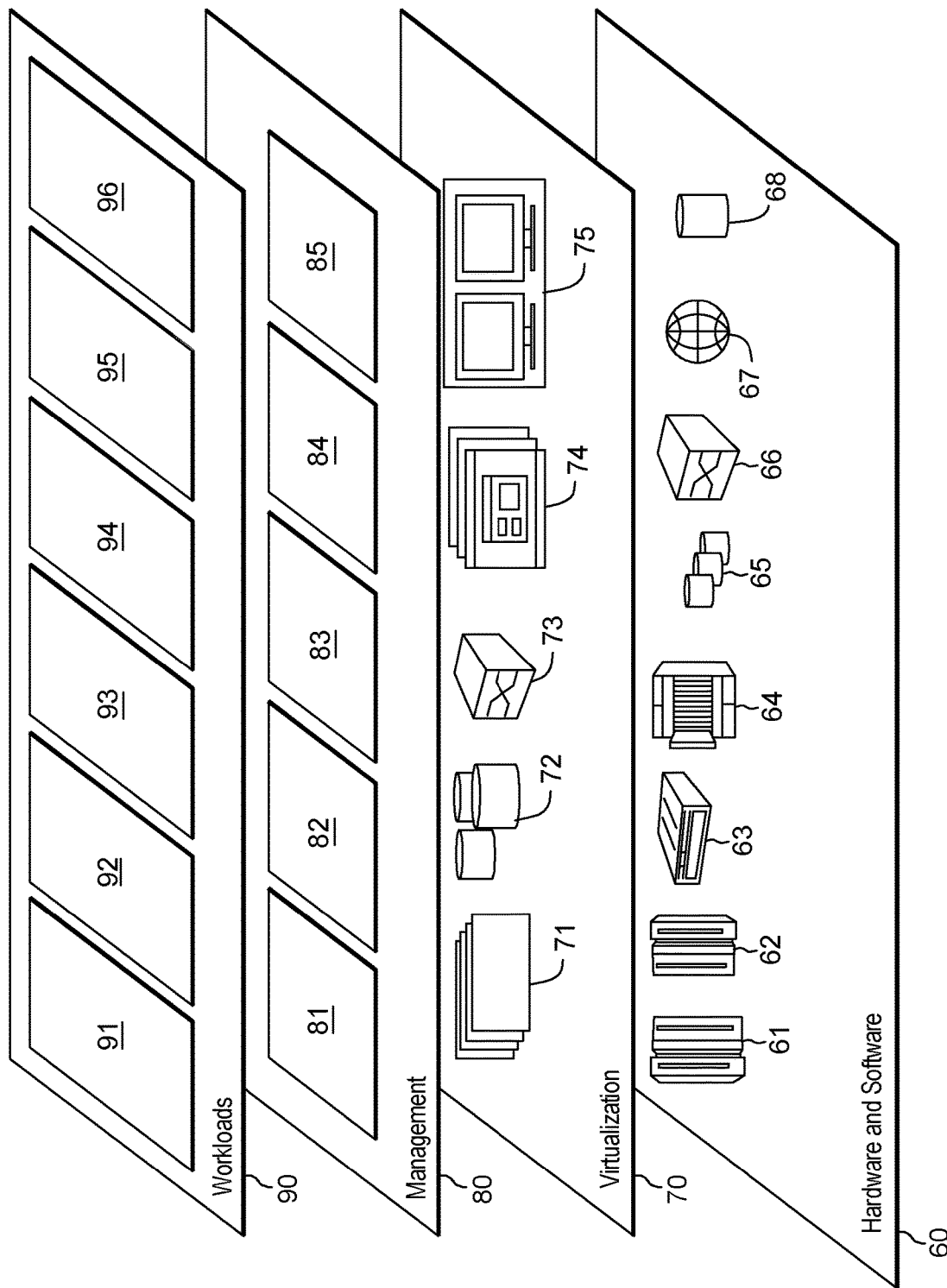
FIG. 11 depicts abstraction model layers according to one embodiment.

FIGS. 9-11 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 9, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 9, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 10-11.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. In one embodiment, manager system 110 can include one or more computing node 10 and can include one or more program 40 for performing functions described with reference to method 200 of FIG. 3 and method 8000 of FIG. 8 and functions described with reference to manager system 110 as set forth in the flowchart of FIG. 4A-4B. In one embodiment, one or more client computer device 130A-130Z can include one or more computing node 10 and can include one or more program 40 for performing functions described with reference to one or more client computer device 130A-130Z as set forth in the flowchart of FIG. 4A-4B. In one embodiment, social media system 140 can include one or more computing node 10 and can include one or more program 40 for performing functions described with reference to social media system 140 as set forth in the flowchart of FIG. 4. In one embodiment, the computing node based systems and devices depicted in FIG. 1, FIG. 2, and FIG. 7 can include one or more program for performing function described with reference to such computing node based systems and devices.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 in one embodiment can include one or more output device 26 connected to bus 18, as may be provided by a haptic output device, and/or an audio speaker. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera, a gyroscope, a temperature sensor, a humidity sensor, a pulse sensor, a blood pressure (bp) sensor or an audio input device. Computer system 12 can include one or more network adapter 20. In FIG. 10 computing node 10 is described as being implemented in a cloud computing environment and accordingly is referred to as a cloud computing node in the context of FIG. 10.

Referring now to FIG. 10, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

Referring now to FIG. 11, a set of functional abstraction layers provided by cloud computing environment 50 (FIG. 10) is shown. It should be understood in advance that the components, layers, and functions shown in FIG. 11 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for stress level determining and responding as set forth herein. The processing components 96 can be implemented with use of one or more program 40 described in FIG. 9.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method comprising:
   obtaining biometric data of a first user, the first user using a first client computer device associated to the first user;

returning a current stress level classification of the first user in dependence on a processing of the biometric data;
generating feedback data in dependence on the current stress level classification of the first user, the feedback data including haptic response feedback data; and
sending the feedback data to a second client computer device of a second user to present feedback to the second user, the feedback being in dependence on the current stress level classification of the first user and including haptic feedback, wherein obtaining and the processing of the biometric data of the first user for return of the current stress level classification of the first user commences in response to the first user and the second user achieving a state of being within a threshold distance of one another and wherein the obtaining and the processing of the biometric data of the first user for return of the current stress level classification of the first user terminates in response to the first user and the second user achieving a state of being separated from one another by more than a distance threshold.

2. The computer implemented method of claim 1, wherein the haptic feedback comprises a vibration having a vibration characteristic that varies in dependence on a level of stress indicted by the current stress level classification.

3. The computer implemented method of claim 1, wherein the haptic feedback comprises a vibration having a vibration strength that varies in dependence on a level of stress indicted by the current stress level classification.

4. The computer implemented method of claim 1, wherein the haptic feedback comprises a vibration having a vibration count that varies in dependence on a level of stress indicted by the current stress level classification.

5. The computer implemented method of claim 1, wherein the processing includes determining a current biometric variance value, the current biometric variance value being a difference between a current biometric data value and baseline biometric data value.

6. The computer implemented method of claim 1, wherein the feedback includes text-based feedback that specifies in text topics determined to reduce a stress level of the first user, and wherein the method includes querying a predictive model trained by supervised machine learning for return of the topics determined to reduce a stress level of the first user.

7. The computer implemented method of claim 1, wherein the obtaining biometric data of the first user includes obtaining output data output by a biometric sensor disposed in the first client computer device.

8. The computer implemented method of claim 1, wherein the first client computer device is a smartwatch worn by the first user, the first client computer device incorporating a biometric sensor for output of the biometric data.

9. The computer implemented method of claim 1, wherein the second client computer device is a smartwatch worn by the second user, the second client computer device incorporating a haptic output device for presentment of the haptic feedback to the second user.

10. The computer implemented method of claim 1, wherein the first client computer device is a smartwatch worn by the first user, the first client computer device incorporating a biometric sensor for output of the biometric data, wherein the second client computer device is a smartwatch worn by the second user, the second client computer device incorporating a haptic output device for presentment of the haptic feedback to the second user.

11. The computer implemented method of claim 1, wherein obtaining and the processing of the biometric data of the first user for return of the current stress level classification of the first user commences in response to the first user breaching a geofence and wherein the obtaining and the processing of the biometric data of the first user for return of the current stress level classification of the first user terminates in response to the first user exiting the geofence.

12. The computer implemented method of claim 1, wherein the feedback includes text-based feedback that specifies in text topics determined to reduce a stress level of the first user, and wherein the method includes querying a predictive model trained by supervised machine learning for return of the topics determined to reduce a stress level of the first user, and wherein training of the predictive model includes iteratively applying training data to the predictive model, wherein the training data includes, for a plurality of time segments, a stress level classification of the first user for a certain time segment associated to conversation topic dataset specifying one or more conversation topic participated in by the first user during the certain time segment.

13. The computer implemented method of claim 1, wherein the feedback includes text-based feedback that specifies in text topics determined to reduce a stress level of the first user, and wherein the method includes querying a predictive model trained by supervised machine learning for return of the topics determined to reduce a stress level of the first user, and wherein training of the predictive model includes iteratively applying training data to the predictive model, wherein the training data includes, for a plurality of time segments, a stress level classification of the first user for a certain time segment associated to conversation topic dataset specifying one or more conversation topic participated in by the first user during the certain time segment.

14. The computer implemented method of claim 1, wherein obtaining and the processing of the biometric data of the first user for return of the current stress level classification of the first user commences in response to the first user breaching a geofence and wherein the obtaining and the processing of the biometric data of the first user for return of the current stress level classification of the first user terminates in response to the first user exiting the geofence, wherein the geofence is established by configuration data entered in a displayed user interface displayed on a display of the second client computer device.

15. The computer implemented method of claim 1, wherein the method includes displaying on a displayed user interface displayed on the second client computer device historical data of the first user, wherein the displayed historical data includes for a certain historical time segment, text specifying a stress level classification of the first user during the certain historical time segment associated to text specifying words of a conversation between the first user and the second user during the certain historical time segment, wherein the user interface permits the second user to view data of historical time segments sorted on the basis of exhibited stress level of the first user that is associated to the time segment, and wherein the displayed historical data for the certain historical time segment is displayed in response to a search entered by the second user into the user interface for data of historical time segments in which the first user exhibited a stress level specified by a data entry of the second user into the user interface.

16. The computer implemented method of claim 1, wherein obtaining and the processing of the biometric data of the first user for return of the current stress level classification of the first user commences in response to the first user breaching a geofence and wherein the obtaining and the processing of the biometric data of the first user for return of the current stress level classification of the first user terminates in response to the first user exiting the geofence, wherein the geofence is established by configuration data entered in a displayed user interface displayed on a display of the second client computer device, wherein the method includes displaying on a displayed user interface displayed on the second client computer device historical data of the first user, wherein the displayed historical data includes for a certain historical time segment, text specifying a stress level classification of the first user during the certain historical time segment associated to text specifying words of a conversation between the first user and the second user during the certain historical time segment, wherein the user interface permits the second user to view data of historical time segments sorted on the basis of exhibited stress level of the first user that is associated to the time segment, and wherein the displayed historical data for the certain historical time segment is displayed in response to a search entered by the second user into the user interface for data of historical time segments in which the first user exhibited a stress level specified by a data entry of the second user into the user interface.

17. The computer implemented method of claim 1, wherein the first client computer device is a smartwatch worn by the first user, the first client computer device incorporating a biometric sensor for output of the biometric data, wherein the second client computer device is a smartwatch worn by the second user, the second client computer device incorporating a haptic output device for presentment of the haptic feedback to the second user, wherein obtaining and the processing of the biometric data of the first user for return of the current stress level classification of the first user commences in response to the first user breaching a geofence and wherein the obtaining and the processing of the biometric data of the first user for return of the current stress level classification of the first user terminates in response to the first user exiting the geofence, wherein the geofence is established by configuration data entered in a displayed user interface displayed on a display of the second client computer device, wherein the method includes displaying on a displayed user interface displayed on the second client computer device historical data of the first user, wherein the displayed historical data includes for a certain historical time segment, text specifying a stress level classification of the first user during the certain historical time segment associated to text specifying words of a conversation between the first user and the second user during the certain historical time segment, wherein the user interface permits the second user to view data of historical time segments sorted on the basis of exhibited stress level of the first user that is associated to the time segment, and wherein the displayed historical data for the certain historical time segment is displayed in response to a search entered by the second user into the user interface for data of historical time segments in which the first user exhibited a stress level specified by a data entry of the second user into the user interface, wherein the feedback includes text-based feedback that specifies in text topics determined to reduce a stress level of the first user, and wherein the method includes querying a predictive model trained by supervised machine learning for return of the topics determined to reduce a stress level of the first user, and wherein training of the predictive model includes iteratively applying training data to the predictive model, wherein the training data includes, for a plurality of time segments, a stress level classification of the first user for a certain time segment associated to conversation topic dataset specifying one or more conversation topic participated in by the first user during the certain time segment.

18. A computer program product comprising:
a computer readable storage medium readable by one or more processing circuit and storing instructions for execution by one or more processor for performing a method comprising:
obtaining biometric data of a first user, the first user using a first client computer device associated to the first user;
returning a current stress level classification of the first user in dependence on a processing of the biometric data;
generating feedback data in dependence on the current stress level classification of the first user, the feedback data including haptic response feedback data; and
sending the feedback data to a second client computer device of a second user to present feedback to the second user, the feedback being in dependence on the current stress level classification of the first user and including haptic feedback, wherein obtaining and the processing of the biometric data of the first user for return of the current stress level classification of the first user commences in response to the first user and the second user achieving a state of being within a threshold distance of one another and wherein the obtaining and the processing of the biometric data of the first user for return of the current stress level classification of the first user terminates in response to the first user and the second user achieving a state of being separated from one another by more than a distance threshold.

19. A system comprising:
a memory;
at least one processor in communication with the memory; and
program instructions executable by one or more processor via the memory to perform a method comprising:
obtaining biometric data of a first user, the first user using a first client computer device associated to the first user;
returning a current stress level classification of the first user in dependence on a processing of the biometric data;
generating feedback data in dependence on the current stress level classification of the first user, the feedback data including haptic response feedback data; and
sending the feedback data to a second client computer device of a second user to present feedback to the second user, the feedback being in dependence on the current stress level classification of the first user and including haptic feedback, wherein obtaining and the processing of the biometric data of the first user for return of the current stress level classification of the first user commences in response to the first user and the second user achieving a state of being within a threshold distance of one another and wherein the obtaining and the processing of the biometric data of the first user for return of the current stress level classification of the first user terminates in response to the first user and the second user achieving a state of being separated from one another by more than a distance threshold.

20. The system of claim 19, wherein the haptic feedback comprises a vibration having a vibration characteristic that varies in dependence on a level of stress indicted by the current stress level classification.

* * * * *